United States Patent
Streit et al.

(10) Patent No.: US 11,229,748 B2
(45) Date of Patent: Jan. 25, 2022

(54) INJECTION APPARATUS COMPRISING A LATERALLY ATTACHED ACTUATION MEMBER FOR TRIGGERING THE PRODUCT RELEASE

(71) Applicant: Ypsomed AG, Burgdorf (CH)

(72) Inventors: Ursina Streit, Schonbuhl (CH); Susanne Schenker, Langenthal (CH); Jürg Hirschel, Bern (CH)

(73) Assignee: Ypsomed AG, Burgdorf (CH)

( * ) Notice: Subject to any disclaimer, the term of this patent is extended or adjusted under 35 U.S.C. 154(b) by 257 days.

(21) Appl. No.: 16/109,192

(22) Filed: Aug. 22, 2018

(65) Prior Publication Data
US 2018/0361072 A1    Dec. 20, 2018

Related U.S. Application Data

(63) Continuation of application No. PCT/CH2017/000010, filed on Feb. 2, 2017.

(30) Foreign Application Priority Data

Feb. 23, 2016    (CH) .................................. 000236/16

(51) Int. Cl.
*A61M 5/31*    (2006.01)
*A61M 5/315*    (2006.01)
*A61M 5/32*    (2006.01)

(52) U.S. Cl.
CPC ...... *A61M 5/31528* (2013.01); *A61M 5/3158* (2013.01); *A61M 5/31553* (2013.01);
(Continued)

(58) Field of Classification Search
CPC ...... A61M 2005/3126; A61M 5/31528; A61M 5/31553; A61M 5/31556; A61M 5/31573; A61M 5/3158; A61M 5/3213
See application file for complete search history.

(56) References Cited

U.S. PATENT DOCUMENTS 5,104,380 A    4/1992    Holman et al.
2012/0136306 A1*    5/2012    Bartha .............. A61M 5/31583
                                                         604/154

(Continued)

FOREIGN PATENT DOCUMENTS

EP           2829292 B1    11/2017
WO        2002053214        7/2002

(Continued)

OTHER PUBLICATIONS

PCT, "International Preliminary Report on Patentability", Application No. PCT/CH2017/000010, dated Aug. 28, 2018, 17 pages.

(Continued)

*Primary Examiner* — William R Carpenter
(74) *Attorney, Agent, or Firm* — Dorsey & Whitney LLP

(57) ABSTRACT

A drive and metering apparatus for an injection apparatus for releasing a liquid product, the drive and metering apparatus comprising: a) a housing, b) a dose adjustment member, which is rotatable relative to the housing for adjusting the product dose to be released, c) an actuation member which is displaceable from a non-actuated position, which it assumes while adjusting the product dose to be released, into an actuated position, which it assumes while it releases the product, wherein the displacement of the actuation member into the actuated position triggers a product release and the actuation member comprises an actuation section, which is accessible to a user of the drive and metering apparatus and by means of which the user can displace the actuation member from the non-actuated position into the actuated position, d) wherein the actuation section is arranged distally in relation to the dose adjustment member.

15 Claims, 20 Drawing Sheets

(52) U.S. Cl.
CPC .... *A61M 5/31556* (2013.01); *A61M 5/31573* (2013.01); *A61M 5/3213* (2013.01); *A61M 2005/3126* (2013.01)

(56) References Cited

U.S. PATENT DOCUMENTS

| | | | |
|---|---|---|---|
| 2013/0281943 A1 † | 10/2013 | Eaton | |
| 2015/0025471 A1 * | 1/2015 | Enggaard | A61M 5/3155 604/189 |
| 2015/0080812 A1 * | 3/2015 | Enggaard | A61M 5/31551 604/211 |
| 2016/0213855 A1 * | 7/2016 | Marsh | A61M 5/20 |

FOREIGN PATENT DOCUMENTS

| | | |
|---|---|---|
| WO | 2007017052 A1 | 2/2007 |
| WO | 2013144020 A1 | 10/2013 |
| WO | 2014166922 A2 | 10/2014 |
| WO | 2015/032771 A1 † | 3/2015 |
| WO | 2015032771 A1 | 3/2015 |
| WO | 2015081451 A1 | 6/2015 |

OTHER PUBLICATIONS

PCT, "International Search Report", Application No. PCT/CH2017/000010, dated May 15, 2017, 7 pages.

\* cited by examiner
† cited by third party

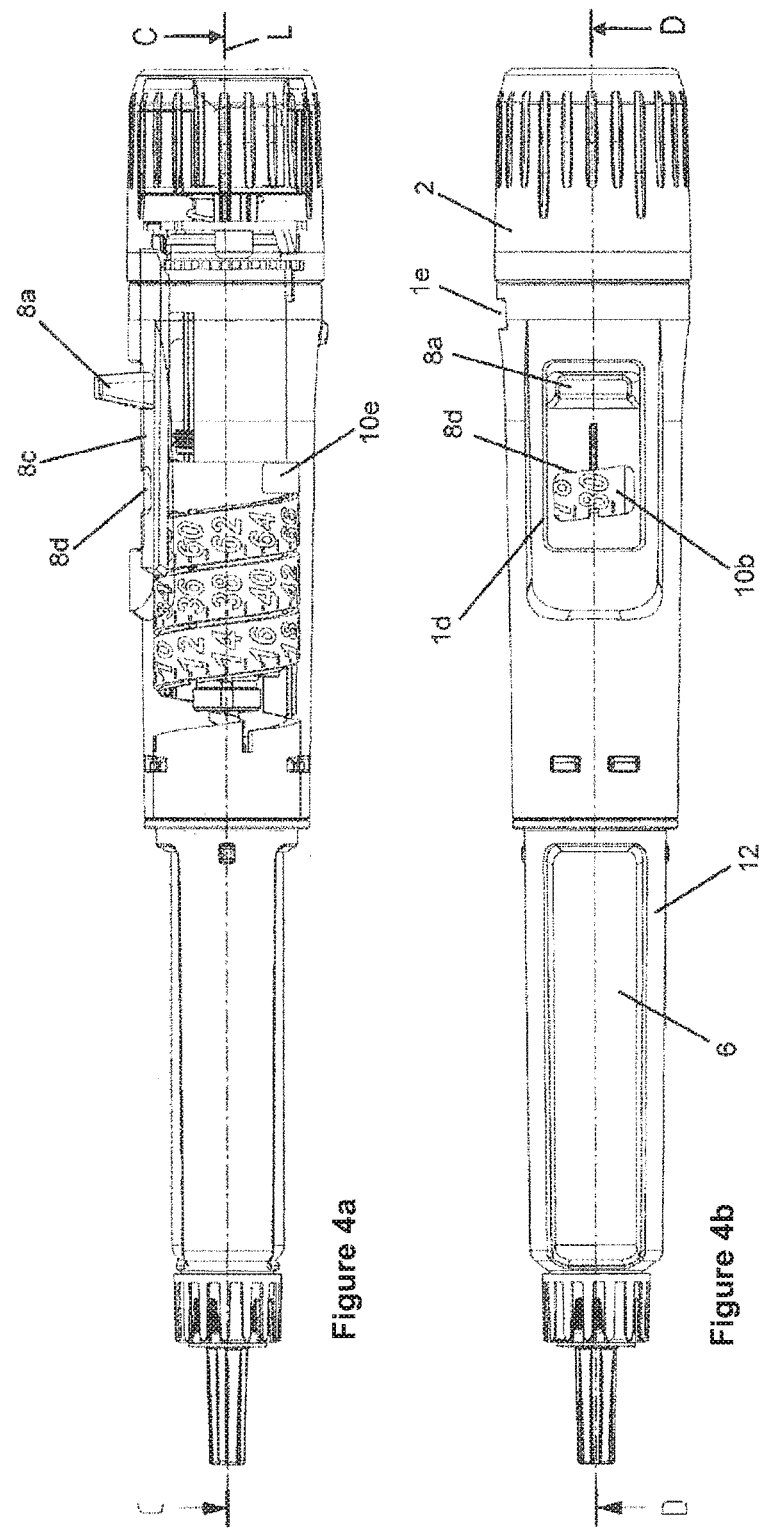

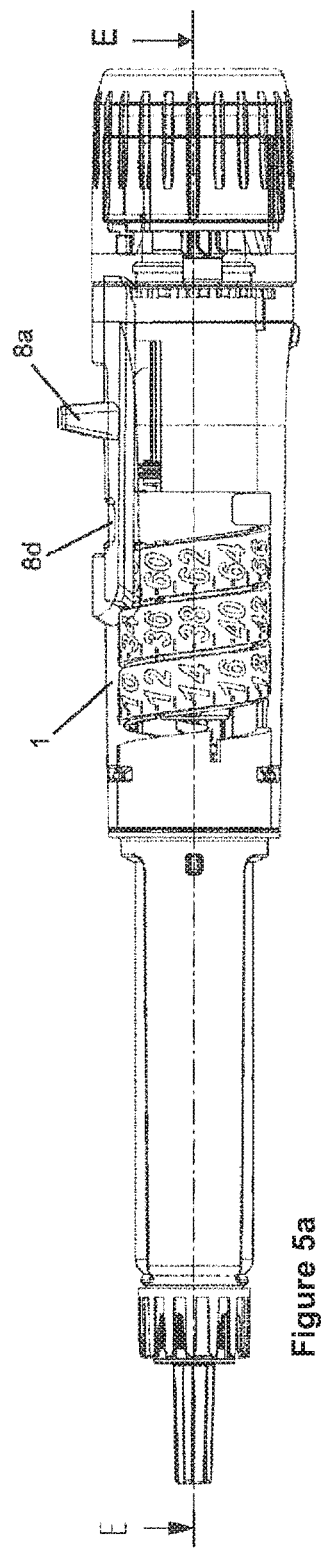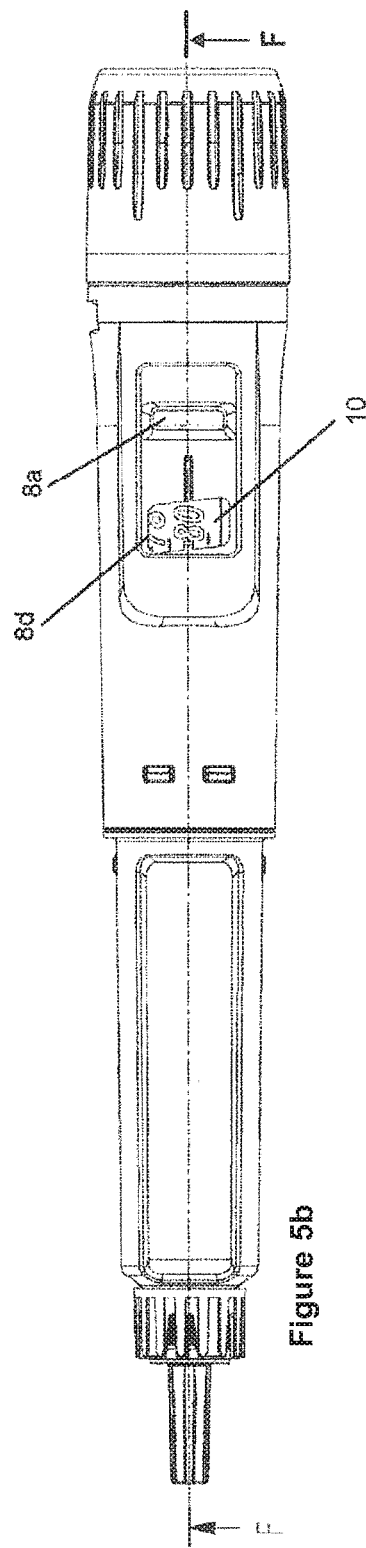

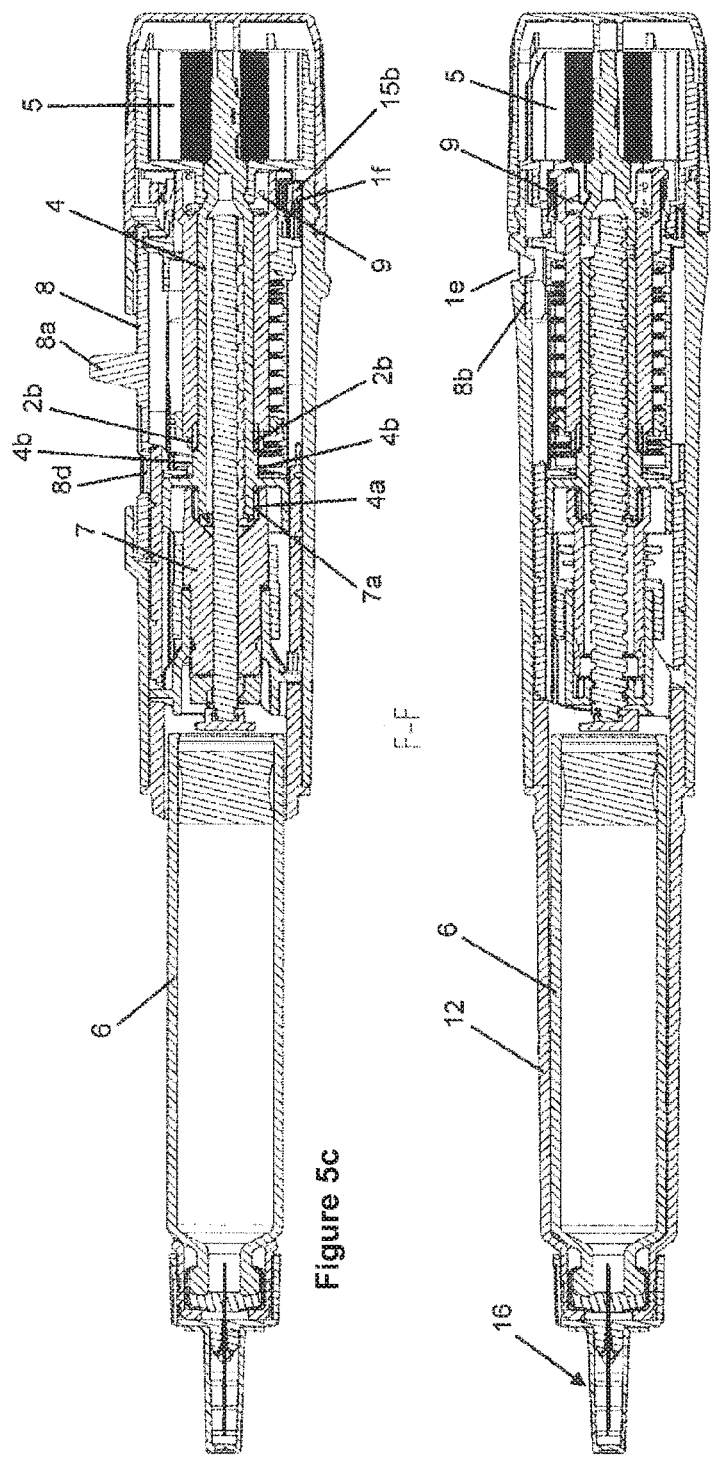

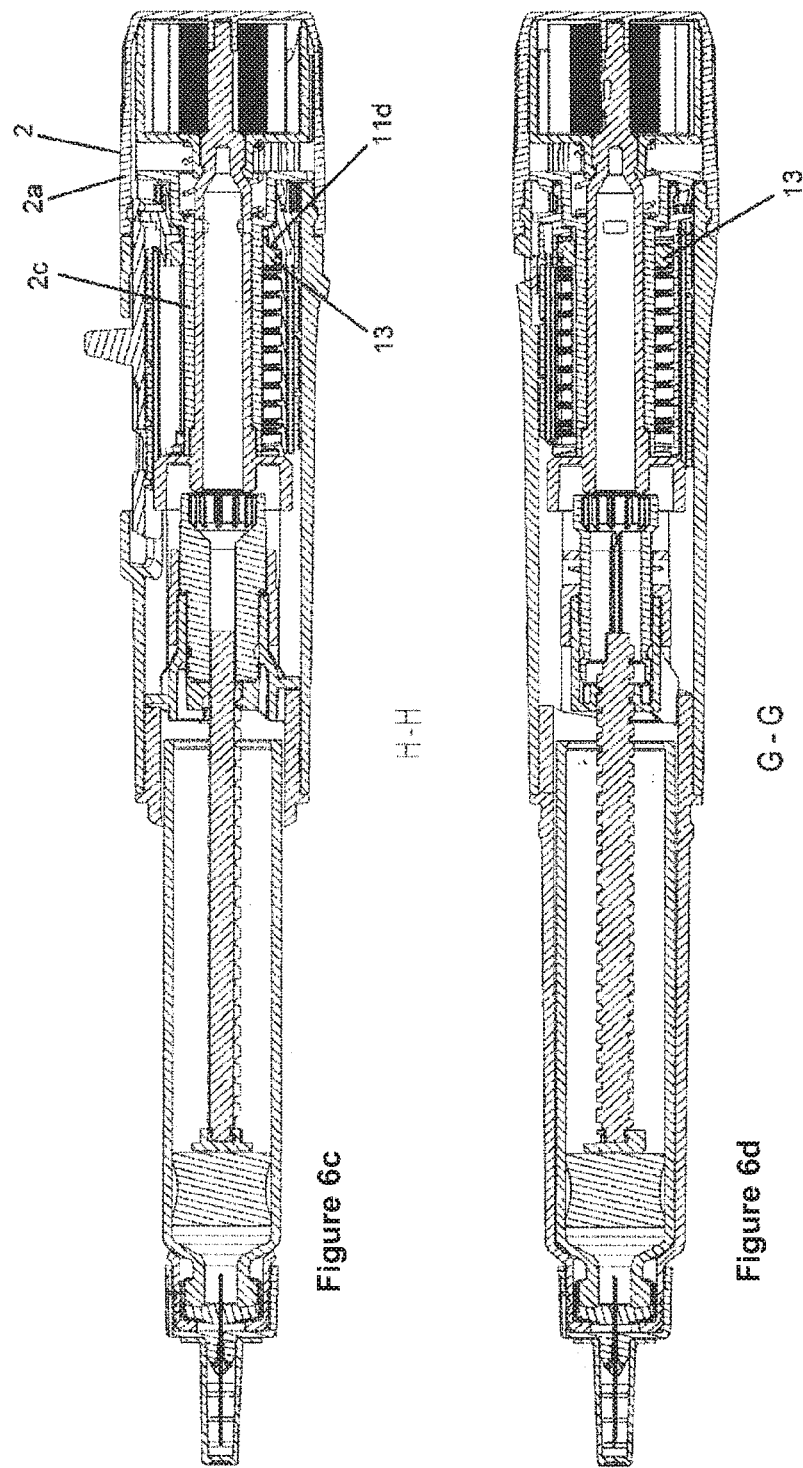

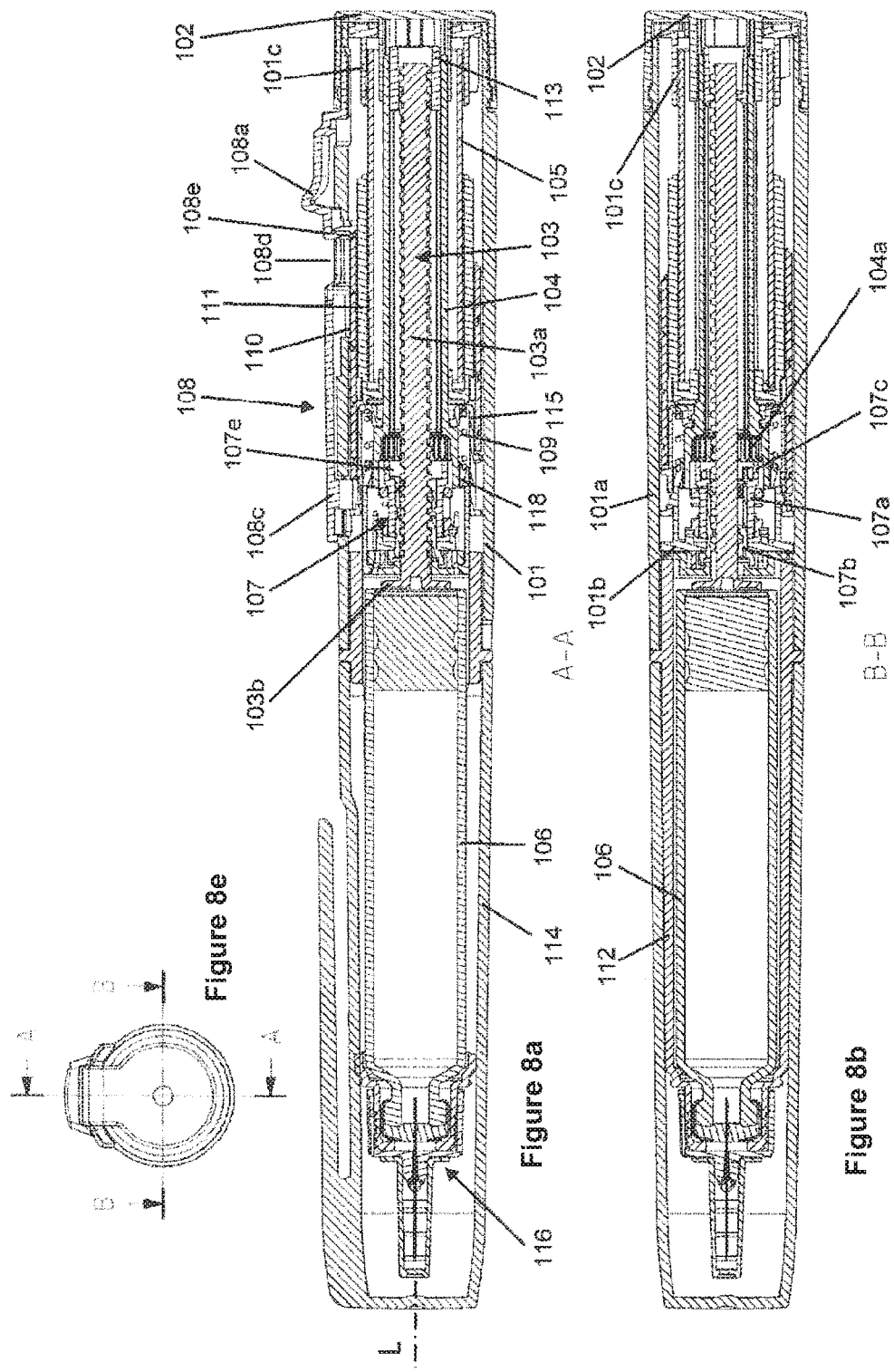

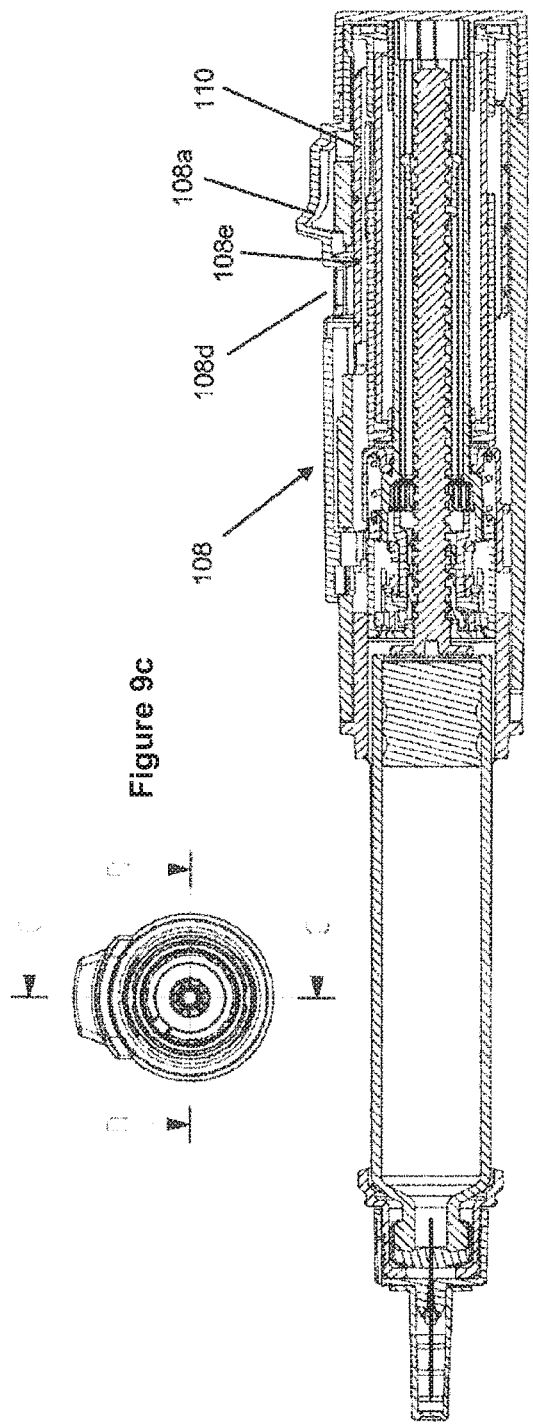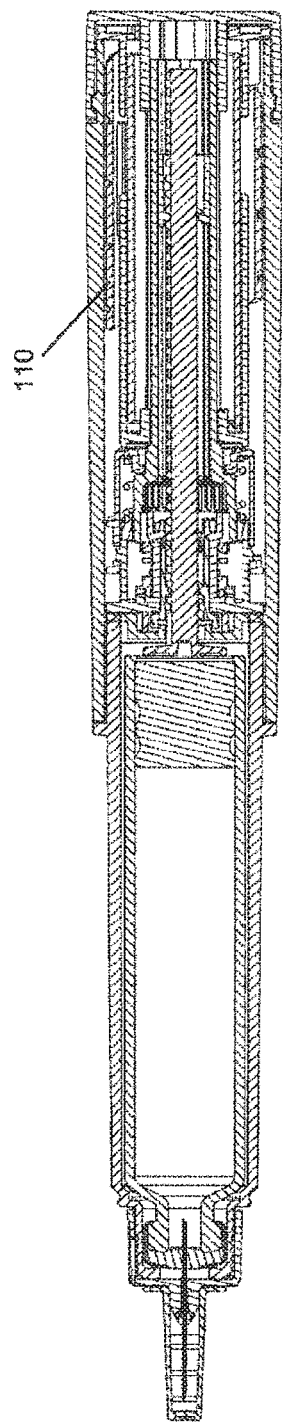
Figure 9a  Figure 9b  Figure 9c

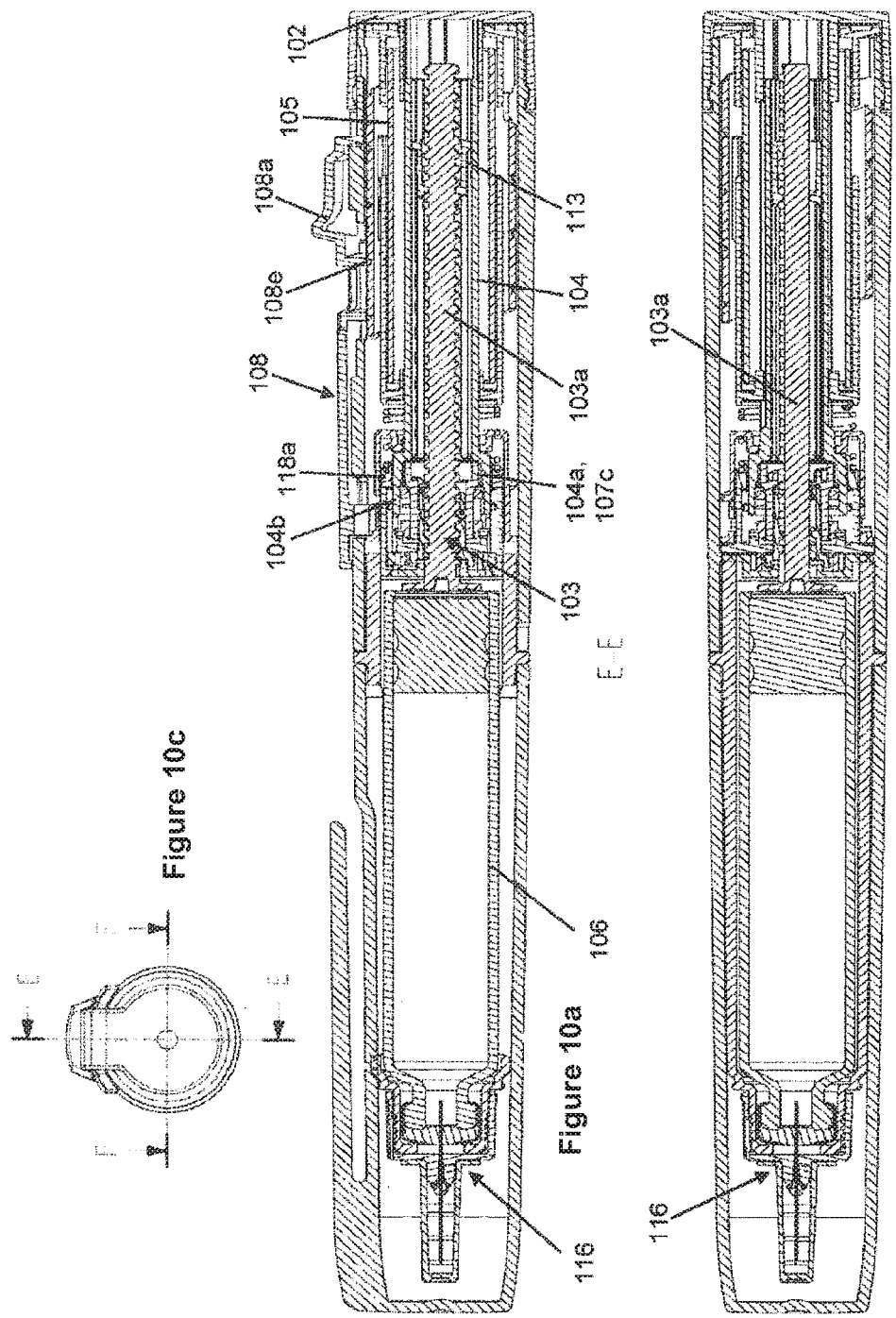

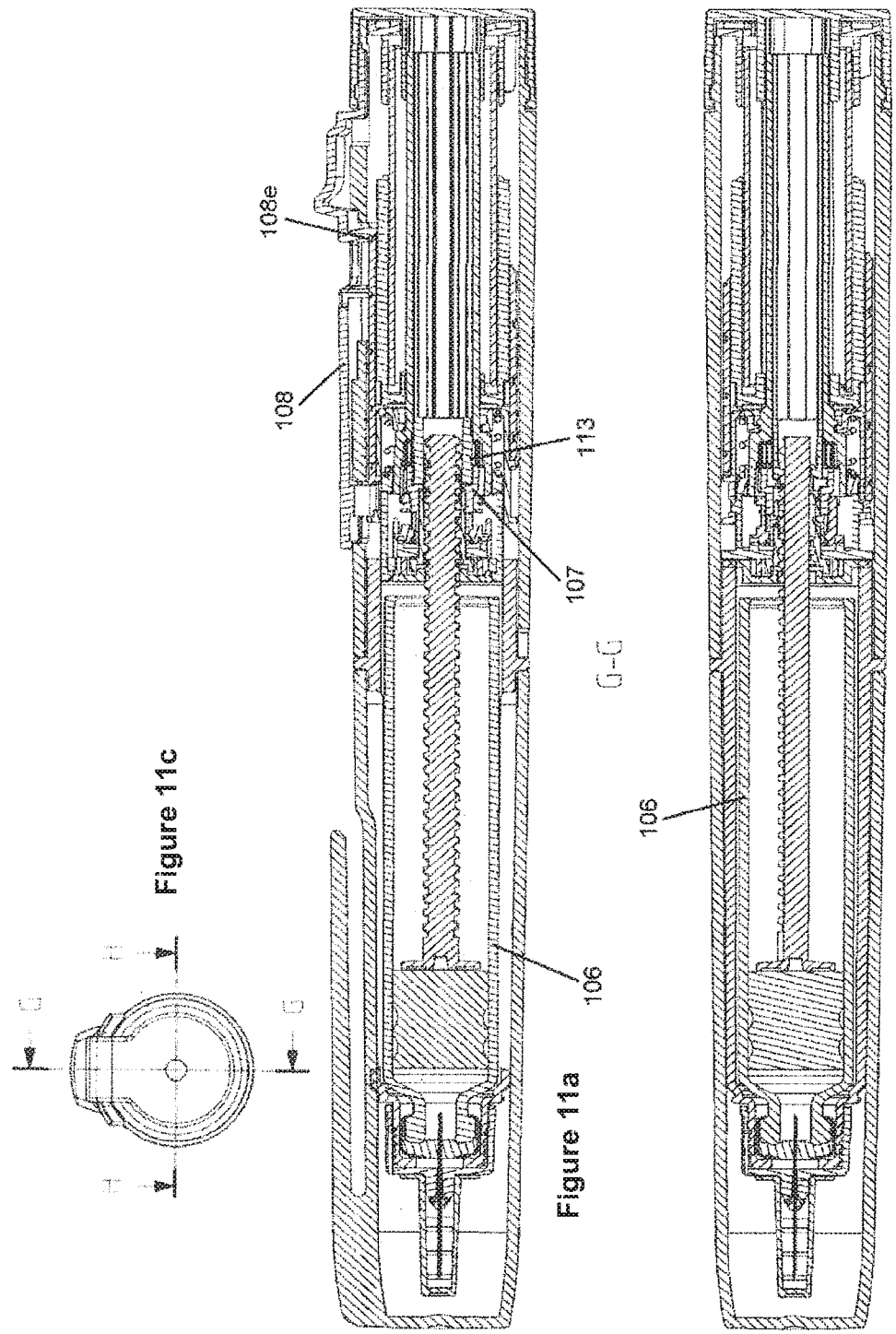

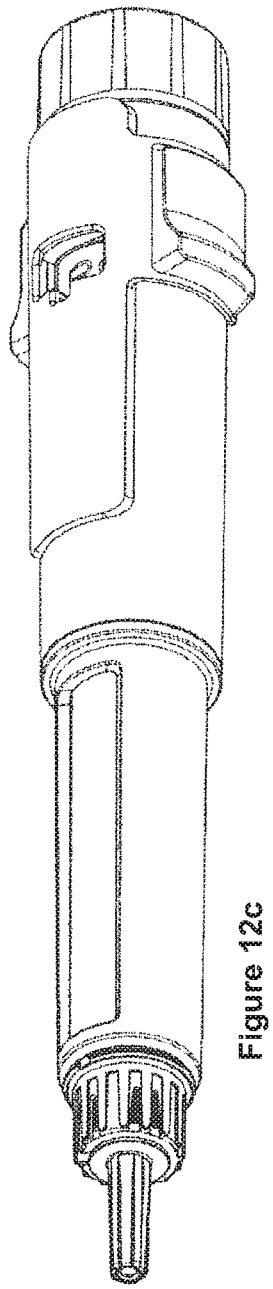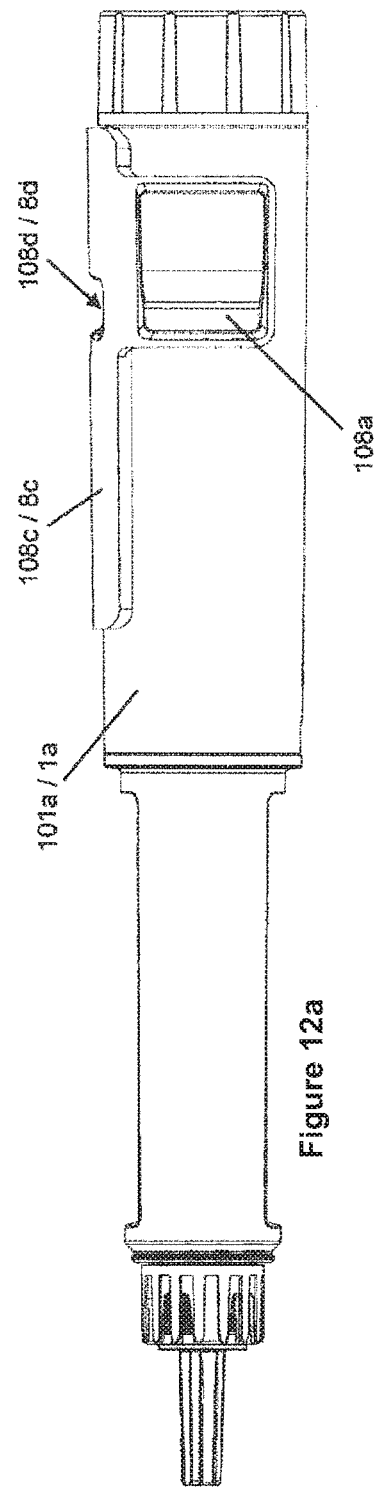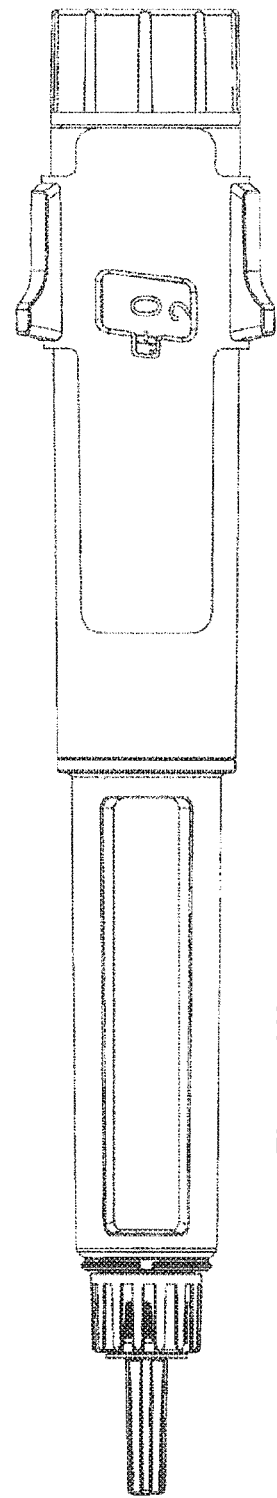
Figure 12c
Figure 12a
Figure 12b

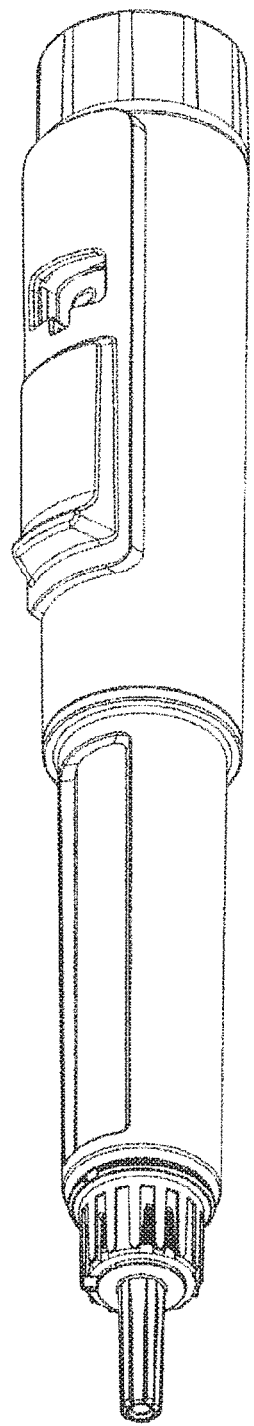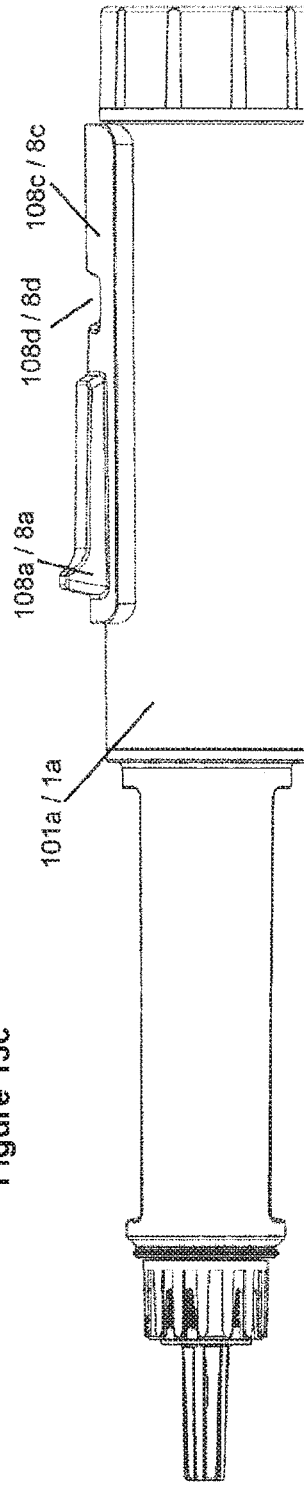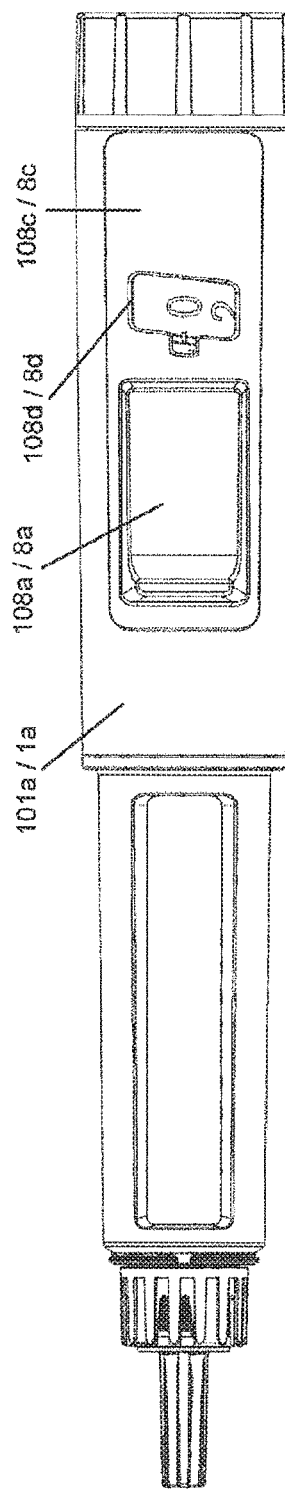
Figure 13c
Figure 13a
Figure 13b

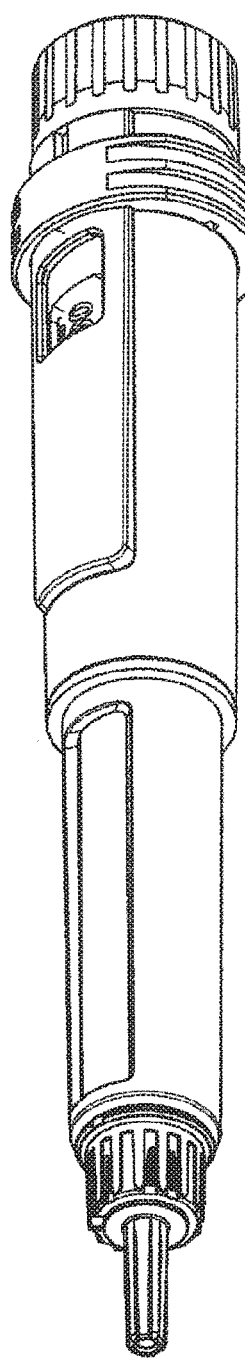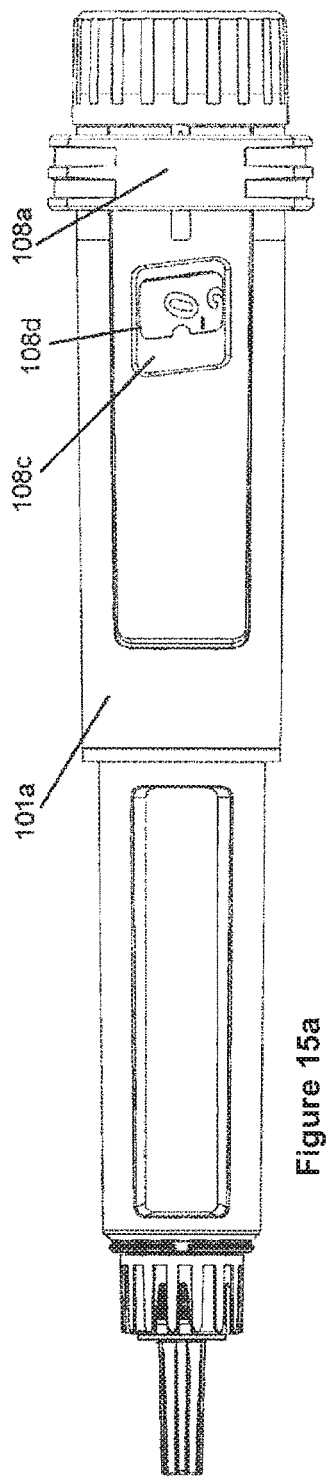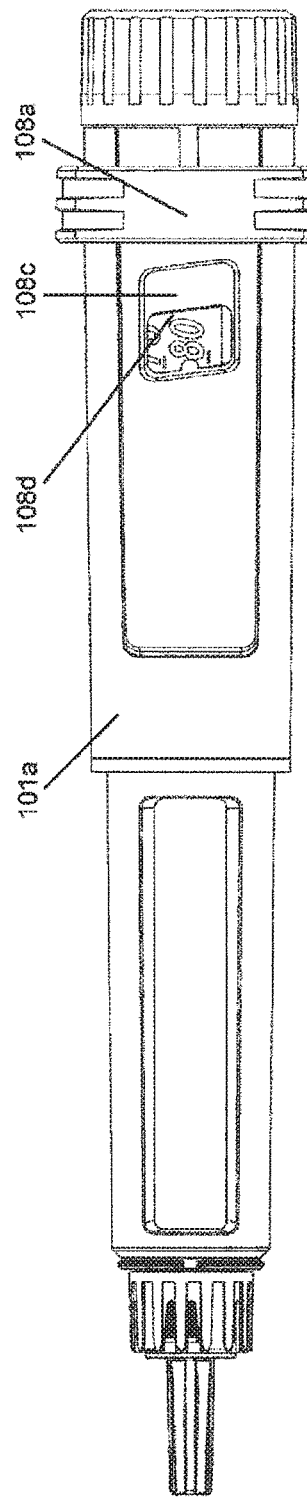
Figure 15c
Figure 15a
Figure 15b

INJECTION APPARATUS COMPRISING A LATERALLY ATTACHED ACTUATION MEMBER FOR TRIGGERING THE PRODUCT RELEASE

CROSS-REFERENCE TO RELATED APPLICATIONS

This application is a continuation of International Application No. PCT/CH2017/000010 filed Feb. 2, 2017, which claims priority to Swiss Application No. 00236/16 filed Feb. 23, 2016, the entire contents of all of which are incorporated by reference herein in their entirety.

BACKGROUND

The invention concerns an injection apparatus for administration of a liquid product, especially a medicament, for example insulin for treatment of diabetes. In detail, the invention concerns a drive and metering apparatus for such an injection apparatus. The drive and metering apparatus comprises an actuation member having an actuation section, which is mounted laterally on the elongated drive and metering apparatus or injection apparatus and which does not form the rear end of the apparatus.

The term "medicament" here comprises any flowable medicinal formulation that is suitable for controlled administration through a means, for example a cannula or hollow needle, for example comprising a liquid, a solution, a gel, or a fine suspension that contains one or more medicinally active agents. Medicament can be a composition having a single active agent or a premixed or co-formulated composition having a plurality of active agents from a single container. Medicament comprises drugs like peptides (for example, insulins, insulin-containing medicaments, GLP-1-containing and derived or analogous preparations), proteins and hormones, biologically obtained or biologically active agents, agents based on hormones or genes, nutritional formulations, enzymes, and other substances, both in solid (suspended) or liquid form, and also polysaccharides, vaccines, DNA or RNA or oligonucleotides, antibodies or parts thereof, and suitable bases, adjuvants, and vehicles.

From the prior art, for example WO 2013/144020 A1, EP 2 829 292 A1, and WO 2015/081451 A1, are known injection apparatuses that have at their proximal end an actuation button, the actuation of which triggers the release of a preset product dose. From U.S. Pat. No. 5,104,380 A1, WO 02/053214 A1, and WO 2007/017052 A1 are known injection apparatuses that have a triggering member laterally mounted on the injection apparatus, the actuation of which triggers a product release.

SUMMARY OF THE INVENTION

It is a problem to make available a drive and metering apparatus for an injection apparatus, where the drive and metering apparatus should afford high user comfort and be easy to manufacture.

The problem is solved with the features of claim 1. Advantageous further developments result from the dependent claims, the description, and the figures.

The invention starts from a drive and metering apparatus for an injection apparatus for administration of a liquid medicament or product. The drive and metering apparatus comprises a housing. The housing is preferably made sleeve-shaped and/or elongated. The housing can, for example, extend along its lengthwise axis, or the lengthwise axis of the drive and metering apparatus.

The housing can optionally accommodate a product container or itself form the product container. The housing can be one-piece or multi-piece. For example, the housing can form a proximal housing part, which essentially forms the drive and metering apparatus, i.e., comprises or has a drive and metering mechanism. The housing can further comprise a product container holder, which accommodates the product container, for example a cartridge, and is connected to the housing or the proximal housing part. Said connection can be such that the product container holder and the housing or the proximal housing part cannot be separated after being connected, i.e., can be separated only by destruction of the connecting elements. Such an embodiment is advantageous in particular for disposable injection apparatuses, which are discarded in their entirety after the product contained in the product container has been completely released. Alternatively, the product container holder can also be separably attached to the housing, through which it is possible to use the drive and metering apparatus a plurality of times, i.e., to exchange an empty product container for a full product container.

The housing preferably serves to be gripped by the user of the apparatus. In particular, the housing can have an essentially cylindrical shape.

The drive and metering apparatus comprises a dose setting member, which is made, for example, as a metering knob. The dose setting member can preferably be gripped by the user (patient, physician, medical personnel) of the drive and metering apparatus and preferably forms an outer surface of the drive and metering apparatus, in particular one that is accessible from outside the drive and metering apparatus. To set the dose to be released or administered, the dose setting member is preferably gripped by the user and rotated relative to the housing about an axis of rotation that preferably corresponds to the lengthwise axis of the drive and metering apparatus, which is designed to elongate, for example. The, for example, sleeve-shaped dose setting member can preferably be connected in an axially fixed way to the housing, in particular cannot be shifted along the lengthwise axis of the housing, through which, advantageously, the intuitive handling of the apparatus by the user is made easier, since one need merely rotate the dose setting member to set the dose.

The dose setting member can, for example, be disposed at the rear end of the housing or the drive and metering apparatus. In particular, the dose setting member can form the rear end of the drive and metering apparatus. By comparison, in the case of WO 2013/144020 A1, EP 2 829 292 A1, and WO 2015/081451 A1 the rear end of the drive and metering apparatus is formed by an actuation member. The dose setting member envisioned for the drive and metering apparatus according to the invention can be closed by means of a rear wall at its rear, i.e., proximal end.

The drive and metering apparatus comprises an actuation member, which can, for example, be sleeve- or shell-shaped (sleeve section). The actuation member serves to trigger the release of the product dose set with the dose setting member. For this, the actuation member can be shifted from an unactuated position, which it takes during the setting of the product dose to be released, to an actuated position, which it takes during the product release. In other words, the shifting of the actuation member from the unactuated position to the actuated position causes triggering of product release. The actuation member is manually actuatable, i.e., by hand, i.e., it can be shifted at least from the unactuated position to the actuated position, for example, and from the actuated position to the unactuated position. Alternatively, the movement from the actuated position to the unactuated position can be undertaken or supported by a reset spring that acts directly or indirectly on the actuation member. The reset spring and the actuation member can be connected to each other, especially indirectly or directly, so that a shifting of the actuation member from the unactuated position causes tensioning of the reset spring and a movement of the actuation member from the actuated position to the unactuated position causes a relaxation of the spring tension.

The actuation member is designed and disposed so that a user of the drive and metering apparatus has access to it. Thus, the actuation member can form an outer surface of the drive and metering apparatus and/or at least a section thereof can be accessible from outside. In particular, at least one actuation section formed by the actuation member can be designed and disposed so that the user of the drive and metering apparatus has access to it, where in particular the actuation member can be shifted from the unactuated position to the actuated position by manipulation or actuation of the actuation section. For example, the actuation section can be disposed so that the user of the drive and metering apparatus can shift the actuation section from the unactuated position to the actuated position with at least one part of the body, in particular at least one finger of the hand which grips the housing of the drive and metering apparatus. For example, the actuation section can be formed by the actuation member in one piece or one part. Generally speaking, the user can shift the actuation member from the unactuated position to the actuated position by means of the actuation section.

For example, the actuation member can advantageously be actuated, in particular pressed, with the thumb of the hand that grips the housing. The actuation can be stopped by releasing the actuation member. "Actuation" means the shifting of the actuation member, in particular along the lengthwise axis of the drive and metering apparatus, for example in the distal direction, so that the product release can be triggered. The actuation member can advantageously be shifted relative to the housing along the lengthwise axis and can, for example, be guided or accommodated in an axially shiftable way by the housing.

The actuation member can advantageously be actuated against the force of the reset or actuation spring, where said spring acts on the actuation member so that it becomes tensioned when the actuation member is shifted from its unactuated position to its actuated position. The actuation member is returned or shifted from its actuated position to its unactuated position by means of the reset spring, in particular with a movement in the proximal direction relative to the housing. The resetting of the actuation member by the spring can, for example, take place by the user releasing the actuation section.

The actuation section can be disposed distal to the dose setting member, which, for example, forms the proximal end, i.e., the end that is opposite the distal end, at which the needle is situated. Accordingly, the dose setting member is disposed proximal to the actuation member, in particular the actuation section. The actuation member, in particular its actuation section, can be disposed between the distal end and the proximal end of the drive and metering apparatus, in particular between the distal end and the dose setting member.

The drive and metering apparatus can comprise a dose display member, for example a dose display drum or at least one dose count ring. The dose display member comprises on its outer circumference a scale running over the circumference, which has scale values that give the set product dose. In the case of a dose display ring, the scale can run over the circumference, where the dose scale in the case of a dose display drum can run in particular in a spiral or helical form over the circumference.

The drive and metering apparatus can comprise a display device, for example a window, which, for example, can be formed as a through-hole or made of a transparent material. The display device can be designed and disposed so that a scale value of the dose scale that corresponds to the set dose can be read through it. The dose display member can, for example, be ring-shaped in cross section. The dose display member can, for example, be a dose display drum or a dose display ring. The dose scale can extend over the circumference of the dose display member, preferably in a spiral. The dose scale preferably comprises a plurality of dose values, which are disposed in order and reveal the dose scale. Preferably, these are numerical values that give the desired product dose in international units (IU) or in mg.

Alternatively, the dose scale can be disposed without a pitch over the circumference of the dose display member, for example the dose display ring, where the scale values then repeat after one rotation of the dose display member. In the case of a dose scale with a pitch, i.e., with a spiral dose scale, the dose display member, in particular the dose display drum, can be rotated more than one rotation without the scale values repeating, so that the scale values can advantageously represent larger or more scale values.

The dose display member can, in particular in the unactuated position of the actuation member, be coupled to the dose setting member, for example directly or indirectly, so that a rotation of the dose setting member causes a rotation of the dose display member. In particular, the dose display member and the dose setting member can be coupled or connected to each other non-rotatably, at least when the actuation member is in its unactuated position. For example, a coupling can be provided, which is kinematically disposed between the dose setting member and the dose display member, where the coupling is connected when the actuation member is in its unactuated position, through which torque can be transmitted from the dose setting member to the dose display member. The coupling can be disconnected when the actuation member is in its actuated position, so that torque cannot be transferred between the dose display member and the dose setting member.

In other words, the product dose to be set can be set via the dose setting member, and the rotation of the dose setting member causes a rotation of the dose display member, so that the set product dose can be read via the display device by means of a scale value from a scale disposed on the outer circumference of the dose display member.

The display device, in particular the window, can be formed by the housing. In further developments of the invention the display device, in particular the window, can be formed by the actuation member, for example its main section. The display device, in particular the window, can thus be shifted along by the shift of the actuation section or the actuation member.

In further developments the actuation member can be coupled to the dose display member so that the dose display member follows the movement of the actuation member when the actuation member is shifted from the unactuated position to the actuated position or shifted back from the actuated position to the unactuated position and back. For example, the dose display member, for example the dose display drum, can have an external thread, which can have a pitch, which corresponds to the pitch of the spiral dose scale. The actuation element, for example a main section of the actuation element, can, for example, engage the external thread of the dose display member by means of an internal thread or at least one threaded section, so that the dose display member is screwed along the actuation element when the dose display member is rotated relative to the actuation element, for example for setting the dose. If the dose display member comprises one or more dose display rings, said ring or rings can be mounted rotatably and axially fixed on the actuation member, in particular on its main section.

The actuation member can be non-rotatable about the lengthwise axis of the drive and metering apparatus and shiftable along the lengthwise axis, with respect to the housing. For this, the drive and metering apparatus, in particular its housing, can comprise a guide, which guides the actuation member non-rotatably and axially shiftable with respect to the housing.

Optionally, the drive and metering apparatus or its housing can have a viewing window, for example an additional viewing window, where the actuation member can have a marking, in particular an actuation marking, disposed within the housing. The marking can be a colored marking, a number, a letter, a pictogram, or the like. The marking can be disposed on the actuation member so that in the unactuated position of the actuation member it is positioned with respect to the viewing window so that it can be read through the viewing window. For example, the marking can be disposed under the viewing window in the line of sight from outside, so that the marking can be seen or read through the viewing window. The marking can be shifted together with the actuation member by shifting the actuation member into the actuated position-into a position with respect to the viewing window in which it can no longer be read through the viewing window. In other words, by shifting the actuation member from the unactuated position, the marking is shifted from the position under the viewing window, so that it is no longer visible. Through this, an additional visual monitoring of the actuation status can be provided to the user.

Alternatively, or in addition to the markings on the actuation member, the dose display member can have a zero dose marking disposed within the housing. The zero dose marking can be a colored marking, a letter, a number, a pictogram, or the like. The zero dose marking can in particular be different from the scale, in particular the scale value that indicates the zero dose in the display device, when, for example, no dose has been set or the dose has been completely released. In particular, the zero dose marking is angularly offset and/or axially offset from the zero value on the scale.

The zero dose marking is disposed on the dose display member so that, when the set dose is zero or the set dose has been completely administered, it is positioned with respect to the viewing window so that it can be read through the viewing window. The viewing window can be the same or a different viewing window from the viewing window in which the marking of the actuation member can be displayed. In particular, when the viewing window is the same viewing window, an additional condition that the zero dose marking is visible can be that the actuation member is in its actuated position, since, for example, the actuation marking can cover the zero dose marking, in particular the zero dose marking is shifted when the actuation marking appears in the viewing window or when the actuation member is in its unactuated position. In this case it is not the zero dose marking that would be displayed, but rather the marking of the actuation member.

The advantage of a zero dose marking that is separate from the dose value "zero" is that the user obtains an additional display indicating whether the product release was completely ended. This can also be advantageous when the actuation section is disposed on the actuation member so that the user of the apparatus would cover the display device with a part of his hand when he actuates the actuation member. In further developments of the invention a plurality of zero dose markings and viewing windows, in particular two, three, or four, can be provided, which are, in particular, uniformly distributed or axially offset over the circumference of the drive and metering apparatus.

The viewing window, in particular the viewing window for the actuation marking of the actuation member and/or the viewing window for the zero dose marking of the dose display member, can be proximal or distal to the actuation section. For example, the viewing window can be mounted on the dose setting member, can be disposed between the actuation section and the dose setting member, or can be disposed between the actuation section and a protective cap. The housing can, for example, have a through-hole, where the actuation section comprises a projection that projects from a main section of the actuation member formed within the housing. The main section can, for example, form the display device and/or be guided lengthwise on the housing. The actuation section can extend through the housing through-hole, where the free end of the actuation section, i.e., the end pointing away from the main section, projects or sticks out beyond the outer circumference of the housing. In this way the user can, for example, actuate the actuation section projecting across the lengthwise direction of the main section, in particular in the distal or proximal direction, with one finger. In this embodiment, for example, the main section can comprise a through-hole, in particular a display device, can be guided on the housing, can be disposed within the housing, and can be in engagement with the dose display member in a manner described herein. Alternatively, the actuation member can be designed so that the user shifts the actuation member across the lengthwise direction, in particular presses across or radially into the housing, in order to trigger the injection device.

In embodiments the housing can have a through-hole, where the main section of the actuation member is disposed outside the housing and is snap-locked to the housing, for example, so that it can be moved axially, i.e., it can be shifted along the lengthwise axis. The actuation section can be a projection projecting outward from the main section, which the user can actuate with a finger. The main section in this embodiment can also form the display device.

The actuation section can be disposed proximal or distal to the display device. That is, the actuation section can be disposed between the display device and the dose setting member or between the actuation member and the distal end of the drive and metering apparatus. An arrangement of the actuation section proximal to the display device has the advantage that the display device can be read more easily during actuation and does not become covered by a part of the hand. The arrangement of the actuation section distal to the display device has the advantage that a longer housing section is available for gripping the drive and metering apparatus with simultaneous release of product with one finger.

The actuation section can be disposed in the circumferential direction or around the lengthwise axis at the same angular position as the display device. This has the advantage that the actuation member is made compact. Alternatively, the actuation section can be disposed in the circumferential direction or around the lengthwise direction angularly offset to the display device. This has the advantage that the display device is more easily read during product release, i.e., it does not become covered by a part of the hand that is gripping the drive and metering apparatus.

The actuation member can surround the housing over its circumference partly, for example over most of it, for example in the form of a ring-shaped section, or completely, for example in the form of a ring. These embodiments have the advantage that the actuation section can be actuated by the user in a plurality of angular positions that the hand can take with respect to the housing. In this way operation becomes easier.

The dose display member can be screwed back and forth between a maximum dose position (maximum dose stop) and a zero dose position (zero dose stop). In the zero dose position, for example, the dose or the figure "zero" can be read in the display device. In the maximum dose position the maximum product dose that can be released with the drive and metering apparatus can advantageously be read.

In the zero dose position the dose display member can be blocked against rotation in one, for example the second, direction of rotation, namely in the direction that would cause a dose less than zero to be set. In the zero dose position the dose display member can, for example, only be moved in the, for example, first direction of rotation, which produces an increase of the dose. In the maximum dose position the dose display member can, for example, be blocked against rotation in a, for example, first direction of rotation, namely in the direction of rotation that would cause a setting of the dose above the maximum settable dose. The dose display member can, in the maximum dose position, be rotated, for example, only in the, for example, second direction of rotation, which produces a reduction of the product dose.

The dose display member can, for example, have a stop, for example a zero dose stop, which in the zero dose position strikes an opposing stop, for example a zero dose opposing stop of the drive and metering apparatus and thus prevents a rotation in the second direction of rotation. The same or an additional stop, for example a maximum dose opposing stop, of the dose display member can prevent the rotation of the dose display member past the maximum dose or in the first direction of rotation by the stop striking a maximum dose opposing stop of the drive and metering apparatus. The dose display member accordingly can have a zero dose stop for the zero dose opposing stop and a maximum dose stop for the maximum dose opposing stop. Preferably, the stop or stops act in the circumferential direction and/or in the axial direction. Additionally, the drive and metering apparatus can have an overload coupling. This has the advantage that if there is an over-rotation of the metering mechanism in which the apparatus is, for example, at a stop, damage to the apparatus is prevented.

The drive and metering apparatus can comprise a driven member accommodated in the housing, for example a threaded or piston rod, the distal end of which can act shiftably on a piston accommodated in the product container, directly or indirectly, for example via a plate-shaped flange mounted at the distal end of the threaded or piston rod, so as to shift the piston to release product. The driven member can carry out a screwing movement directed in the distal direction, in particular about the lengthwise axis, for example to release product. For this, the piston or threaded rod can have an external thread on its circumference, which engages in a thread of the housing or an element fixed to the housing, so that a rotation of the piston or threaded rod brings about a screwing movement of the piston or threaded rod.

Alternatively, the piston or threaded rod can have a lengthwise guide, for example a lengthwise slot or at least one flattened side, in which an engagement element of the housing or the element fixed to the housing engages, so that the piston or threaded rod is secured against rotation with respect to the housing but can be shifted axially. In this way the driven member carries out a purely axial movement (without rotary movement) for the product release.

The drive and metering apparatus can, for example, comprise a drive spring, in particular a tensionable or tensioned drive spring, which stores the energy necessary for a product release and can release the energy to a drive member and thus also to the driven member. The drive spring in one variation can be coupled to the dose setting member so that the drive spring becomes tensioned by rotation of the dose setting member, in particular in a direction of rotation that causes an increase of the dose (first direction of rotation). Optionally, the drive spring can become untensioned or not untensioned through rotation of the dose setting member in the rotation direction that ensures a dose decrease (second direction of rotation). If the spring does not become untensioned, between the dose setting member and the spring there can be disposed a ratchet, which ensures that the spring can only be tensioned, but no longer untensioned, by rotation of the dose setting member, In an alternate variation the drive spring can be a pretensioned drive spring, which, for example, is so highly tensioned that the spring energy stored in it is sufficient to completely release the product from a completely filled product container in one or more releases. For this, the drive spring can be disposed so that a rotation of the dose setting member does not produce any tensioning or relaxation of the spring. That means that in the rotation of the dose setting member in the first direction of rotation, which causes an increase of dose, no tensioning of the spring takes place (and also no relaxation) and by rotation of the dose setting member in the second direction of rotation, which causes a decrease of dose, no relaxation (and also no tensioning) of the spring is produced.

The drive and metering apparatus can comprise a drive member, which can be rotated relative to the housing and preferably about the lengthwise axis and which during the product release or when the actuation member is actuated is coupled to the driven member so that a rotation of the drive member causes the driven member to be moved in the distal direction relative to the housing. One end of the drive spring, which can also be called a rotational or torsion spring, can be fixed to the drive member or can abut the drive member. The at least one drive spring, which serves as release spring, can be a helical or screw spring, which acts as a rotary or torsion spring. Especially preferably, the drive spring can be a spring wound in a helical shape from a strip-shaped material, especially metal, which can be called, for example, a helical or clock spring. A rotationally tensioned spring tries to rotate the parts that rest against it relative to each other. The other end of the spring can rest directly or indirectly against the housing, an element fixed to the housing, the dose setting member, or at least one element that is rotationally fixed in a direction with the dose setting member, for example a spring housing.

For example, a rotational member can be kinematically disposed between the drive member and the driven member.

The preferably sleeve-shaped rotational member can surround the driven member. The rotational member is preferably connected to the housing or an element fixed to the housing in an axially fixed and rotatable way. Preferably, the housing or an element fixed to the housing and the rotational member engage so that the rotational member is rotatable and axially fixed relative to the housing, i.e., cannot be shifted along the lengthwise axis.

In a first variation the rotational member can be in a threaded engagement with a thread of the driven member. For example, the driven member can have an internal thread and the rotational member an external thread, which mesh together. Preferably, the rotational member can have an internal thread and the driven member, especially its threaded rod, can have an external thread, which mesh with each other.

The driven member, for example its threaded rod, can be in engagement with a guide of the drive and metering apparatus fixed to the housing. For example, the guide fixed to the housing can be a lobe or a non-round cross section, which engages in a slot or a non-round cross section, for example at least one flattened side, of the driven member. For example, the slot or the non-round cross section can extend parallel to the lengthwise axis of the elongated driven member. The guide fixed to the housing can be formed by the housing itself or a part connected rotationally or axially fixed to the housing. Said part can be connected permanently to the housing or can be connected to the housing rotationally and axially fixed at least during product release. The slot or the non-round cross section of the driven member can, as an alternative to the embodiment in which it extends parallel to the longitudinal axis, extend helically or spirally about the lengthwise axis, but with a different pitch than the thread. Said variation results in a rotation of the rotational member causing a movement of the driven member in the distal direction, in particular when the rotational member is rotated in the second direction of rotation relative to the housing. Here the driven member can either screw in the distal direction, in particular when the slot or the non-round cross section of the driven member is helical, or can shift linearly, in particular when the slot or the non-round cross section extends parallel to the lengthwise axis.

In a second variation an internal thread fixed to the housing can be in a threaded engagement with an external thread of the driven member, in particular its threaded rod. The driven member, in particular the threaded rod, and the rotary member can mesh with each other so that the driven member is non-rotatable relative to the rotary member and can be shifted along the lengthwise axis. A rotation of the rotary member produces a screwing movement of the driven member in the distal direction. The driven member can have a non-round cross section or a slot which extends along or parallel to the lengthwise axis and is in engagement with a non-round cross section or a projection of the rotary member.

Generally preferably, a rotation of the drive member in the second direction of rotation relative to the housing and/or the dose setting member, during product release or when the actuation member is activated, causes the driven member to move relative to the housing in the distal direction. In particular, a rotation of the drive member relative to the housing and/or the dose setting member causes the rotary member, which is kinematically disposed between the drive member and the driven member, to rotate together with the drive member, i.e., relative to the housing and/or the dose setting member. The rotation of the rotary member in the second direction of rotation produces a movement of the driven member in the distal direction. The driven member is moved relative to the housing in the distal direction in particular only during product release.

The drive and metering apparatus can, for example, comprise a first coupling, which is disposed, in particular kinematically, between the drive member and the driven member. In particular, the first coupling can be disposed between the drive member and the rotational member. The first coupling is uncoupled during the setting of the product dose or if the actuation member is not actuated, so that the drive member can be rotated relative to the driven member. During product release or when the actuation member is actuated, the first coupling is coupled. In particular, this results in the rotational member and the drive member being connected non-rotatably. The rotational member can thus be rotated together with the drive member, for example in the second direction of rotation.

The first coupling can comprise a first coupling structure, which is non-rotatably coupled to the drive member, in particular formed by the drive member, and a second coupling structure, which is coupled non-rotatably to the rotational member, in particular formed by the rotational member. The first coupling structure can be or comprise a gear, where the second coupling structure can be or comprise a gear. The gears of the first coupling structure and the second coupling structure can mesh together in a form fit when the first coupling is coupled. For example, the first coupling structure can be an internal gear, and the second coupling structure can be an external gear. Alternatively, the first coupling structure can be an external gear, and the second coupling structure can be an internal gear.

The actuation member can be connected—directly or indirectly—with the first coupling structure, for example in an axially fixed way, so that the first coupling structure can be shifted together with the actuation member, through which the first coupling is coupled by shifting the actuation member from the unactuated position to the actuated position, i.e., the first coupling structure is shifted into engagement with the second coupling structure.

The drive and metering apparatus can comprise, for example, a second coupling, which in particular serves to keep the drive spring from becoming untensioned in an uncontrolled way. The second coupling can be disposed between, in particular kinematically, the dose setting member and the drive member. The second coupling is coupled during the setting of the product dose or when the actuation member is unactuated, so that the dose setting member and the drive member are secured against rotation with respect to each other. The second coupling can comprise a third coupling structure, which is connected non-rotatably to the dose setting member, in particular is formed by the dose setting member, and a fourth coupling structure, which is connected non-rotatably with the drive member, in particular is formed by the drive member.

In another embodiment the second coupling can be disposed between, in particular kinematically, the drive member and the housing, an element fixed to the housing, or an element that meshes together in a form fit into the housing or the element fixed to the housing and is separable from said form-fit engagement by rotating it relative to the housing, for example, a coupling member. The second coupling is coupled during the setting of the product dose or when the actuation member is unactuated, so that the drive member is non-rotatable relative to the coupling member. The coupling member can comprise an engagement structure and the housing can comprise a cooperating engagement structure, which mesh together in a form fit, in particular can be pressed axially into engagement by an elastic means, for example a spring, where the engagement structure and the cooperating engagement structure and possibly the elastic means are matched to each other so that for rotation of the coupling member in the first direction of rotation a first limit torque acting on the coupling member in the first direction of rotation must be exceeded and for rotation of the coupling member in the second direction of rotation a second limit torque acting on the coupling member in the second direction of rotation must be exceeded. The first limit torque can be smaller than the second limit torque. The matching is such that the second limit torque is greater than the torque with which the drive spring can be maximally tensioned by means of the drive and metering apparatus, i.e., the torque that the drive spring provides when the maximum dose stop and the maximum dose opposing stop contact each other. In this way the torque provided by the drive spring by itself is not sufficient to rotate the coupling member in the second direction of rotation relative to the housing, but instead twisting in the second direction of rotation is possible only with an additional torque acting in the second direction of rotation, which, for example, is applied to the dose setting member by the user. This prevents an uncontrolled relaxation of the drive spring. The second coupling can comprise a third coupling structure, which is connected non-rotatably to the coupling member, in particular is formed by the coupling member, and a fourth coupling structure, which is connected non-rotatably to the drive member, in particular is formed by the drive member.

During the product release or when the actuation member is actuated, the second coupling is uncoupled, so that the drive member can be rotated relative to the dose setting member, in particular in the second direction of rotation, by means of the tensioned drive spring.

The third coupling structure can be or can comprise a gear, where the fourth coupling structure can be or can comprise a gear. The gears of the third coupling structure and the fourth coupling structure can mesh together in a form fit when the second coupling is coupled. The third coupling structure can be an internal gear, and the fourth coupling structure can be an external gear. Alternatively, the third coupling structure can be an external gear, and the fourth coupling structure can be an internal gear.

The fourth coupling structure can be connected to the actuation member in an axially fixed way, so that the fourth coupling structure follows the movement of the actuation member. In particular, the fourth coupling structure can be moved out of engagement with the third coupling structure by shifting the actuation member from the unactuated position to the actuated position, so that the second coupling becomes uncoupled.

The first and second couplings can be matched to each other, for example, so that the actuation member can take, for example first, an intermediate position between the unactuated position and the actuated position, in which the first coupling is coupled and the second coupling is coupled. This has the advantageous effect that the rotation of the drive member by the drive spring can only be released when it is certain that the rotational member is coupled non-rotatably to the drive member. Advantageously, a malfunction of the apparatus that could occur if the first coupling is not yet coupled and the second coupling has already been uncoupled, is avoided in this way.

For example, a unidirectional coupling, for example a ratchet, which permits rotation of the rotational member relative to the housing in the, for example, second direction of rotation and which blocks the other, for example first, direction of rotation, can be disposed between the rotational member and the housing or an element fixed to the housing. Preferably, the unidirectional coupling permits the rotation of the rotational member relative to the housing in the direction that causes the movement of the driven member in the distal direction.

Optionally, the drive and metering apparatus can comprise a third coupling, which can be disposed between, in particular kinematically, the dose setting member and the housing. The third coupling is uncoupled during the setting of the product dose or when the actuation member is unactuated, so that the dose setting member can rotate relative to the housing. During the product release or with the actuation member actuated, the third coupling is coupled, so that the dose setting member is non-rotatable relative to the housing. Generally, it is preferred that the dose setting member be non-rotatable relative to the housing. This has, on the one hand, the advantageous effect that during the product release a dose adjustment is not possible and on the other hand the drive spring can support by a section directly against the housing.

The third coupling can be formed between the dose setting member or the spring housing and the housing, where it is preferred that the spring housing and the dose setting member be connected non-rotatably, in particular permanently non-rotatably, or at least non-rotatable during the setting of the product dose and during the product release.

The third coupling can comprise a fifth coupling structure, which is connected non-rotatably to the housing, in particular formed by the housing, and a sixth coupling structure, which is connected non-rotatably to the dose setting member, in particular formed by the dose setting member or the spring housing that is connected non-rotatably to the dose setting member. The fifth coupling structure can comprise or be a gear, where the sixth coupling structure can comprise or be a gear. The gears of the fifth coupling structure and the sixth coupling structure can mesh together in a form fit when the third coupling is coupled. The fifth coupling structure can be an external gear, and the sixth coupling structure can be an internal gear. Alternatively, the fifth coupling structure can be an internal gear and the sixth coupling structure can be an external gear. The sixth coupling structure can be connected or coupled in an axially fixed way to the actuation member, so that the sixth coupling structure follows the movement of the actuation member along the lengthwise axis. In particular, the sixth coupling structure can be shifted into engagement with the fifth coupling structure by shifting the actuation member from its unactuated position to the actuated position, in particular while shifting the spring housing relative to the dose setting member, so that the sixth coupling structure and the fifth coupling structure mesh in a non-rotatable way about the lengthwise axis.

The drive member can be connected to the dose display member, preferably non-rotatably and with the possibility of being shifted axially. In particular, the dose display member and the drive member can mesh together non-rotatably and axially shiftable or can be connected via a, for example, sleeve-shaped intermediate member, where the intermediate member and the dose display member mesh together non-rotatably and axially shiftable and where the intermediate member and the drive member mesh together non-rotatably and axially shiftable. The drive spring can, for example, be affixed to the intermediate member at one end, and the other end of the drive spring can be affixed to the housing or an element fixed to the housing.

Further, the drive and metering apparatus can comprise a last dose device, which prevents a dose that exceeds the amount of product contained in the product container from being set. The device then only comes into effect when the amount of product contained or releasable from the product container is less than the dose that can be set by the drive and metering apparatus. The last dose device can preferably comprise a stop element and an opposing stop; in particular, the stop element can contact the opposing stop when the amount of product that is contained in the product container or that can be released from it is less than the dose that can be set with the drive and metering apparatus. In this case the user can no longer rotate the dose setting member to a dose that is greater than the residual amount that is contained in the product container or that can be released, and the torque is transferred from the dose setting member via the drive device to the stop element and the opposing stop, where the opposing stop is connected non-rotatably to the housing.

As noted above, the drive and metering apparatus can comprise an overload or safety coupling in order to prevent damage to the apparatus in the case of over-rotation of the dosing member, in which the apparatus is, for example, at a stop (zero dose stop, maximum dose stop, or last dose stop). The overload coupling can preferably be mounted between the dose setting member and the drive device. The overload coupling can be a ratchet, or a spring-type slip coupling, or a latching mechanism, which separates a coupling upon an overload. If the user rotates the dose setting member further, even though the drive and metering apparatus is at one of the stops (zero dose stop, maximum dose stop, or last dose stop) and the transmitted torque exceeds a permissible limit, the overload coupling becomes activated and the drive and dosing member are separated from each other before elements loaded by the torque become damaged. The invention was described by means of a number of preferred embodiments. Below especially preferred embodiments of the invention are described by means of the figures. The features disclosed in doing so form the invention individually and advantageously further in any combination of features.

BRIEF DESCRIPTION OF THE DRAWINGS

FIGS. 4a-4d show various views of the apparatus in FIG. 1 set to the maximum dose and with an unactuated actuation member.

FIGS. 5a-5d show various views of the apparatus in FIG. 1 set to the maximum dose and with an actuated actuation member.

FIGS. 6a-6d show various views of the apparatus in FIG. 1 in a state in which the product container of the apparatus has been completely emptied and the actuation member is unactuated.

FIGS. 8a-8e show various views of the embodiment in FIG. 7 in an initial state. FIG. 8e illustrates an axial cross-section view showing lines A-A and B-B, which identify the locations of the longitudinal cross-sectional views of FIGS. 8a and 8b, respectively.

FIGS. 9a and 9b show different views of the embodiment in FIG. 7 set to the maximum dose and with an unactuated actuation member.

FIG. 9c illustrates axial cross-section view showing lines A-A and B-B, which identify the locations of the longitudinal cross-sectional views of FIGS. 9a and 9b, respectively.

FIGS. 10a and 10b show different views of the embodiment in FIG. 7 set to the maximum dose and with an actuated actuation member.

FIG. 10c illustrates axial cross-section view showing lines A-A and B-B, which identify the locations of the longitudinal cross-sectional views of FIGS. 10a and 10b, respectively.

FIGS. 11a and 11b show different views of the embodiment in FIG. 7 in a state in which the product container of the apparatus has been completely emptied and the actuation member is unactuated.

FIG. 11c illustrates axial cross-section view showing lines A-A and B-B, which identify the locations of the longitudinal cross-sectional views of FIGS. 11a and 11b, respectively.

FIGS. 12a and 12b show views of an injection apparatus according to a third embodiment that are rotated 90° with respect to each other about the lengthwise axis.

FIG. 12c shows a perspective view of the third embodiment of an injection apparatus.

FIGS. 13a and 13b show views of an injection apparatus according to a fourth embodiment that are rotated 90° with respect to each other about the lengthwise axis.

FIG. 13c shows a perspective view of the fourth embodiment of an injection apparatus.

FIGS. 15a and 15b show views of an injection apparatus according to a sixth embodiment that are rotated 90° with respect to each other about the lengthwise axis.

FIG. 15c shows a perspective view of the sixth embodiment of an injection apparatus.

DETAILED DESCRIPTION

Figure 1:
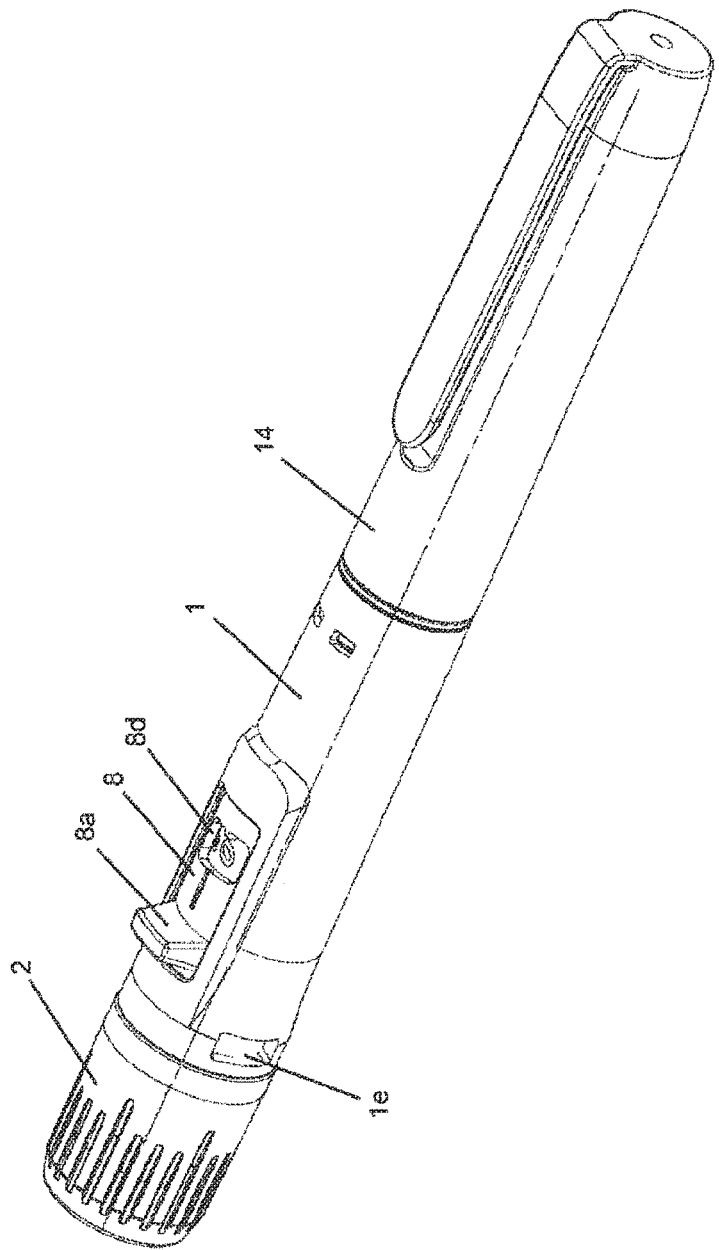
FIG. 1 shows a perspective view of a first embodiment of an injection apparatus.
Figure 2:
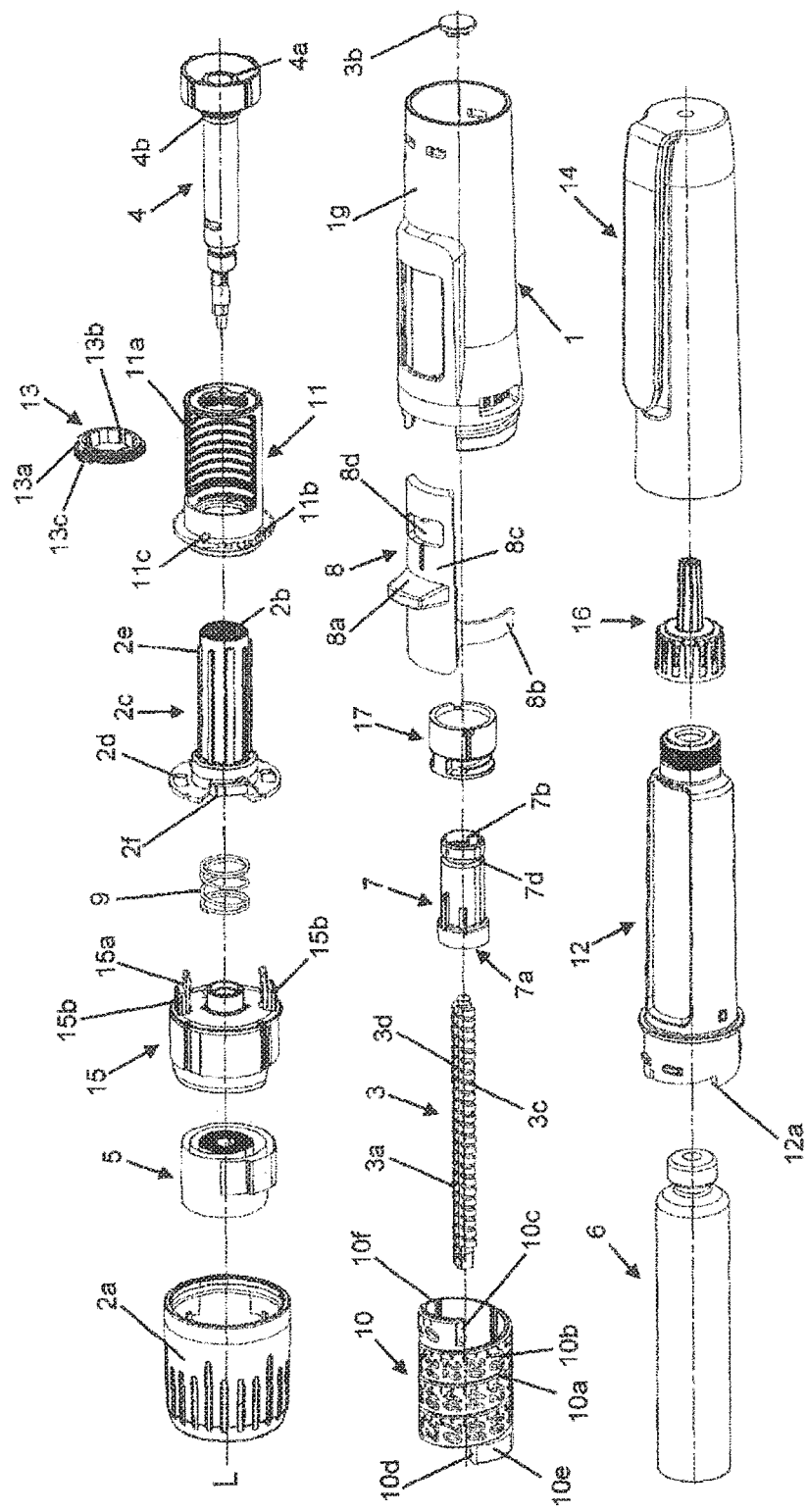
FIG. 2 shows an exploded view of the individual parts of the apparatus in FIG. 1.
Figure 3A:
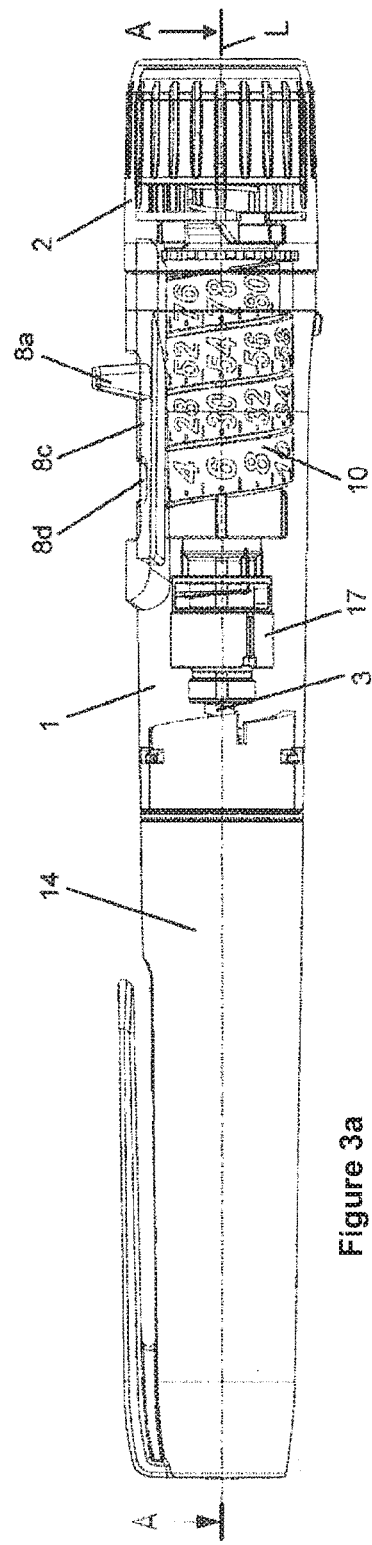
FIGS. 3a-3d show different views of the apparatus in FIG. 1 in an initial state.
Figure 3B:
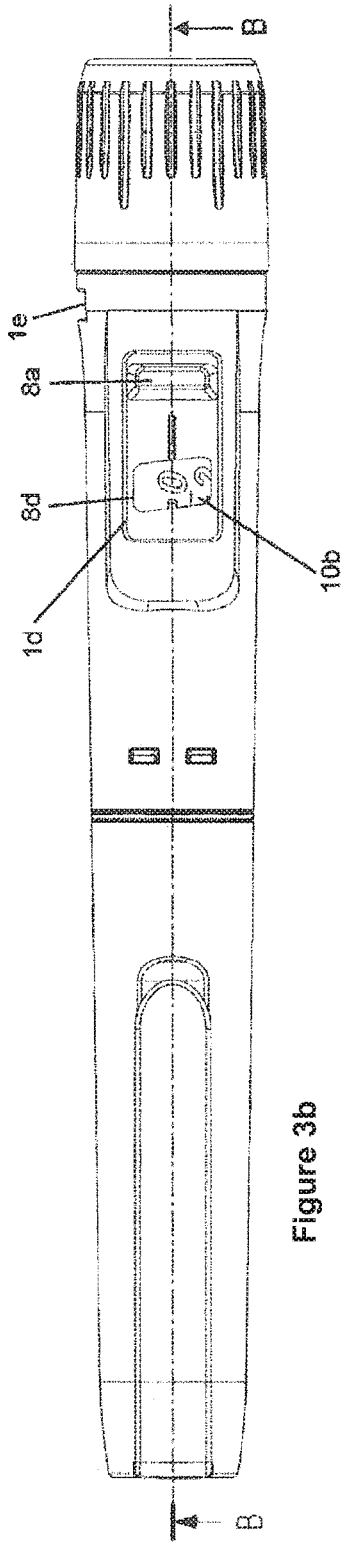
Figures 3C, 3D:
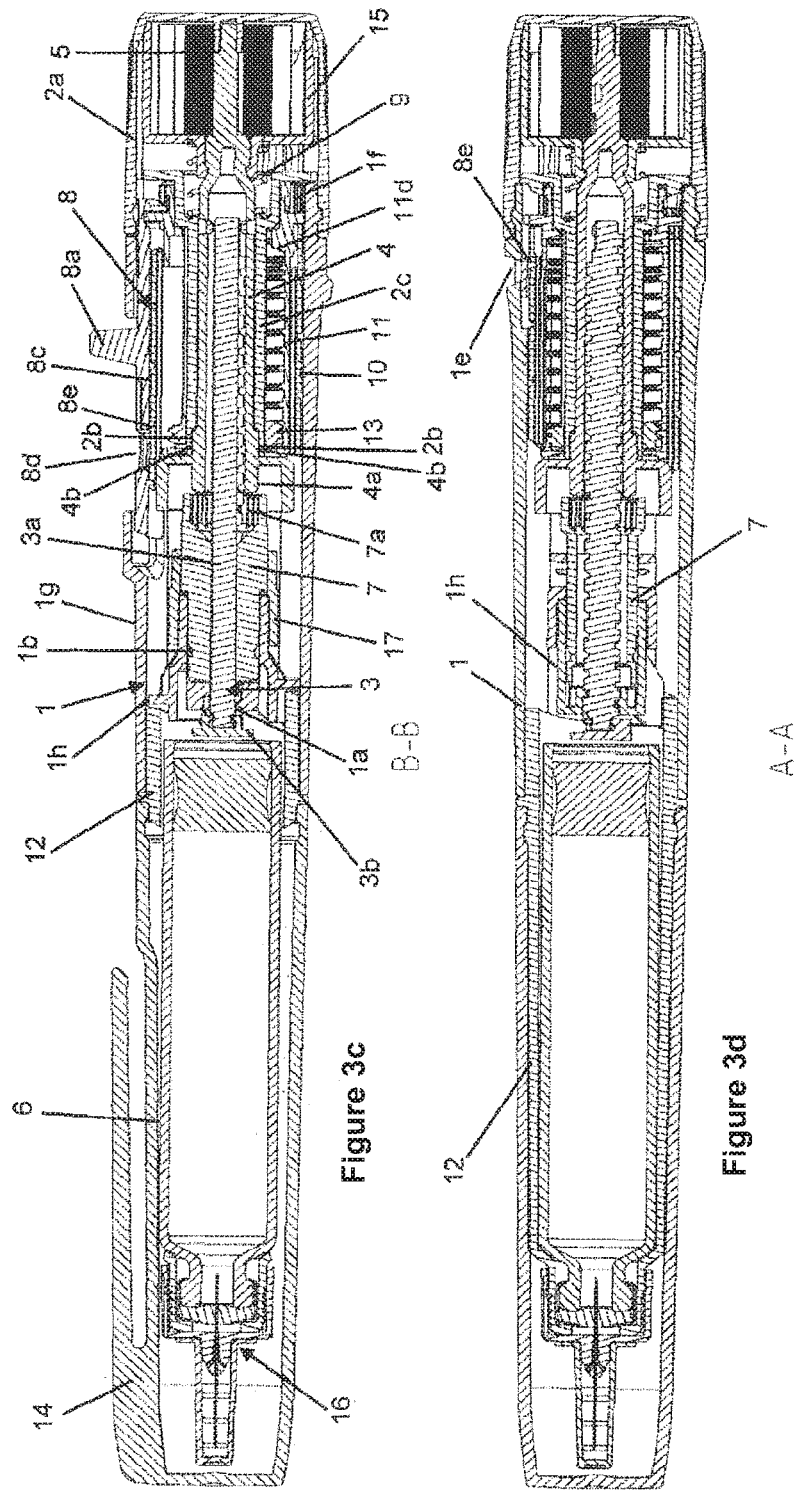
Figures 4C, 4D:
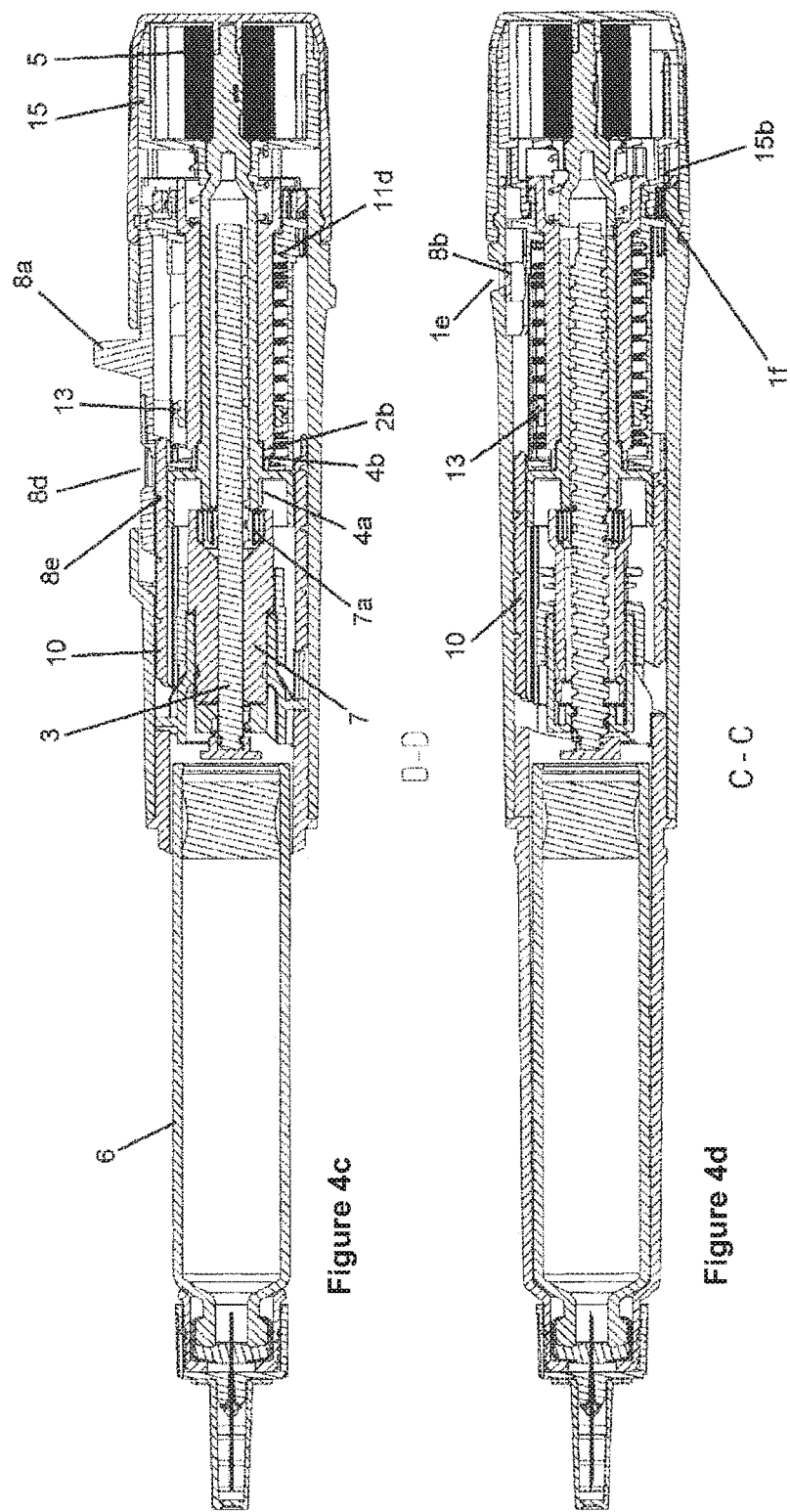
Figure 6A:
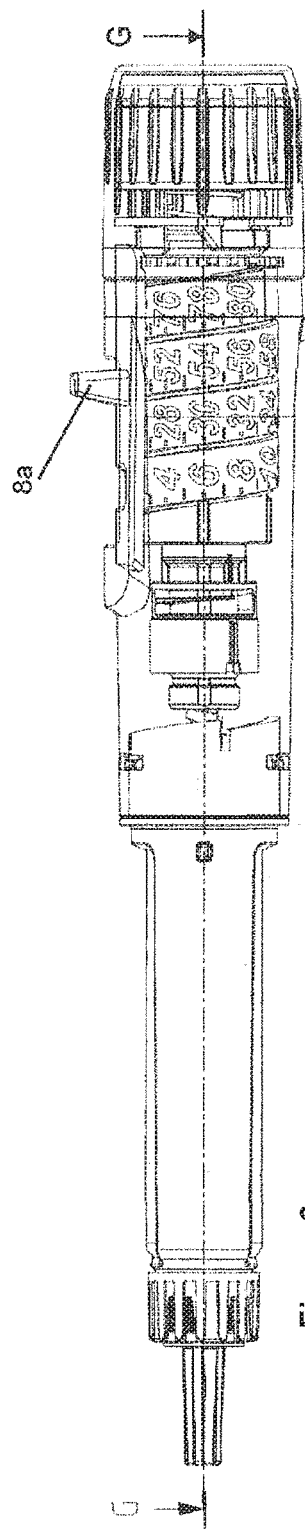
Figure 6B:
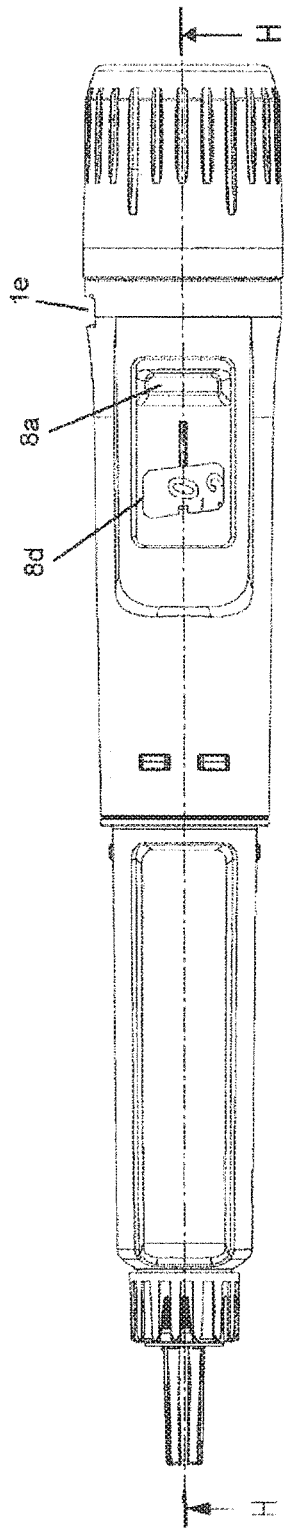
Figure 7:
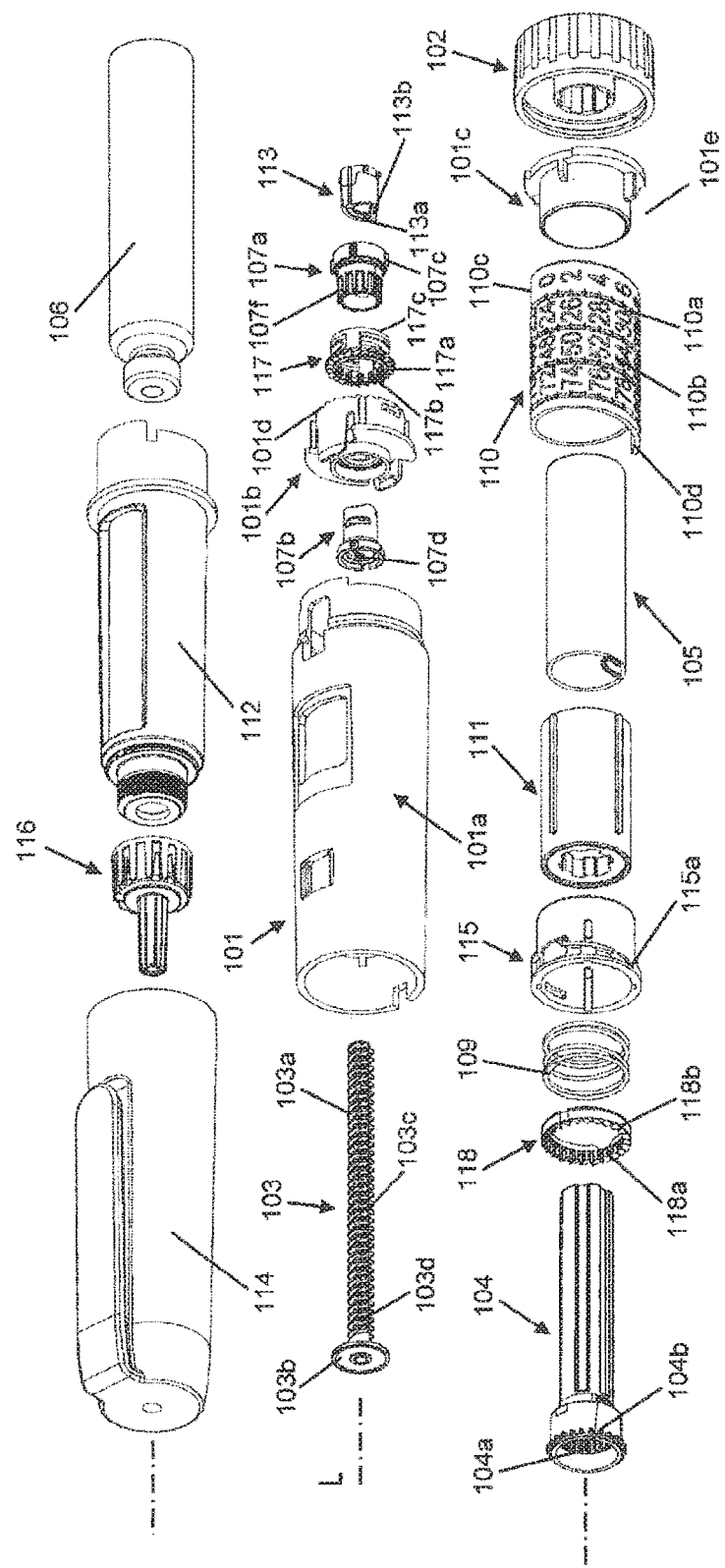
FIG. 7 shows an exploded view of the individual parts of a second embodiment of an injection apparatus.
Figure 8C:
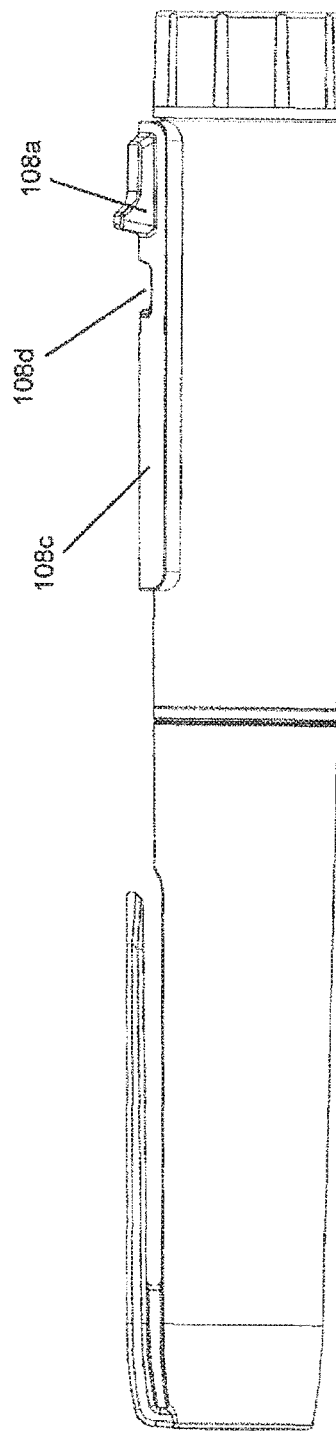
Figure 8D:
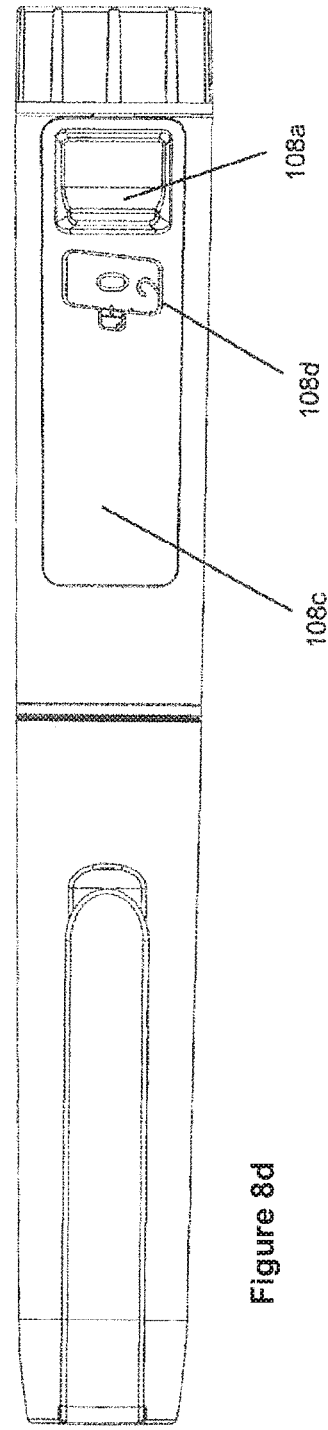

The first embodiment shown in FIGS. 1 to 6d and the second embodiment shown in FIGS. 7 to 11b overlap only partly in their mode of operation. The actuation members 8, 108 shown in the first to sixth embodiments can be used in the case of each of the first and second embodiment, i.e., each of the first and second embodiment can be modified with any of the actuation members 8, 108 described herein. The drive and metering apparatus forms an injection apparatus or is at least a part of such an injection apparatus.

The drive and metering apparatus of the first embodiment in FIGS. 1 to 6d has a sleeve-shaped housing 1, which comprises an outer sleeve 1g and an inner sleeve 1h which is connected and concentrically disposed thereto. The inner sleeve 1h is connected, in particular snapped together, with the outer sleeve 1g non-rotatably and axially fixed. Alternatively, the outer sleeve 1g could be made in one part with the inner sleeve 1h. The inner sleeve 1h and the outer sleeve 1g are firmly connected via a ring-shaped ridge formed by the inner sleeve 1h. The housing 1, in particular the inner sleeve 1h, has an internal thread 1a, which engages in an external thread 3c of a threaded rod 3a of a driven member 3, so that the threaded rod 3a and thus the driven member 3 can be screwed in the distal direction relative to the housing 1 and along a lengthwise axis L. The driven member 3 comprises the threaded rod 3a and a plate-shaped flange 3b which is affixed to the distal end of the threaded rod 3a in a freely rotatable way, in particular is snapped together with it. The threaded rod 3a comprises at least one guide slot 3d, which overlays the external thread 3c and extends parallel to the lengthwise axis L. A sleeve-shaped rotational member 7 comprises, on its internal circumference, at least one engagement member 7b, which engages the guide slot 3d, so that the rotational member 7 and the driven member 3 can shift axially and non-rotatably relative to each other. The rotational member 7 comprises, on its external circumference, a ring-shaped slot 7d, in which a projection 1b formed on the internal circumference of the housing 1, in particular the inner sleeve 1h, engages, so that the rotational member 7 is rotatable relative to housing 1 and is axially fixed. A rotation of the rotational member 7 produces a rotation of the driven member 3, so that the driven member 3 can move along the lengthwise axis L because of the threaded engagement with the housing 1. For example, the driven member 3 is moved in the distal direction when the rotational member 7 is rotated in a second direction of rotation about the lengthwise axis L relative to the housing 1. A unidirectional coupling 17, which allows rotation of the rotational member 7 in the second direction of rotation and prevents rotation in the first direction of rotation, is kinematically disposed between the housing 1, in particular the inner sleeve 1h, and the rotational member 7. Therefore, the rotational member 7 cannot rotate in the first direction of rotation, for example because of vibrations or the like, which would cause the driven member 3 to move in the proximal direction. The unidirectional coupling 17 can additionally be designed so that the rotational member, for rotation in the second direction of rotation, must preferably overcome a certain, but small torque, which prevents vibrations from causing a rotation of the rotational member 7 in the second direction of rotation. The unidirectional coupling 17 can additionally be designed as a signaling device, which produces an acoustic and/or tactile signal (click) if the rotational member 7 is rotated in the second direction of rotation and thus signals the product release. The unidirectional coupling 17 in this example is sleeve-shaped and surrounds a part of the inner sleeve 1h and a part of the rotational member 7. The inner sleeve 1h and the unidirectional coupling 17, which is designed as a ratchet, are connected non-rotatably to each other, and the second unidirectional coupling 17 and the rotation member 7 mesh together by means of an elastic means formed either by the rotational member 7 or by the unidirectional coupling 17, for example a click arm, where the part that does not form the click arm preferably comprises a gear, via which the click arm can rest, where the gear comprises, for example, sawtooth teeth, which result in the elastic means being able to slide over the gear teeth only in one direction and blocking such sliding of the teeth in the opposite direction. Alternatively, the unidirectional coupling 17 can be connected non-rotatably to the rotational member 7, and the unidirectional coupling 17 could then be connected to the inner sleeve 1h by means of the elastic means and the gear.

The rotational member 7 comprises a second coupling structure 7a in the form of an internal gear, which is formed in particular at the proximal end of the rotational member 7.

An outer sleeve 2a of a dose setting member 2 is affixed to the proximal end of the housing 1, in particular the outer sleeve 1g, rotatable and axially fixed. The outer sleeve 2a comprises on its internal circumference an annular slot running about the lengthwise axis L, in which an engagement member formed on the external circumference of the outer sleeve 1g engages, so that the outer sleeve 2a and thus the dose setting member 2 is affixed to the housing 1 rotatable and axially fixed. The outer sleeve 2a comprises a structured surface at its outer circumference to simplify the rotation of the outer sleeve 2a relative to the housing 1 for the user of the apparatus. The dose setting member 2 forms the proximal end of the drive and metering apparatus, or the injection apparatus. The proximal end of the outer sleeve 2a is closed. The outer sleeve 2a can, as shown here, be pot shaped, where the bottom of the pot forms the proximal end of the injection apparatus and the side wall of the pot forms the outer sleeve 2a.

The dose setting member 2 comprises an inner sleeve 2c, and the inner sleeve 2c and the outer sleeve 2a engage with each other at least non-rotatably and optionally axially shiftable or axially fixed. The inner sleeve 2c can optionally be made in one piece with the outer sleeve 2a. The inner sleeve 2c is connected to the outer sleeve 2a via a collar in its proximal region. The collar comprises at least one through-hole 2d, here two through-holes 2d, and an arm 15a projecting distally from a spring housing 15 extends through the at least one through-hole 2d. A stop element 13, e.g., stop ring, surrounding the inner sleeve 2 and the inner sleeve 2 mesh together non-rotatably and axially shiftable. For this the inner sleeve 2c comprises on its outer circumference at least one lengthwise fin 2e, which extends along the lengthwise axis L. The ring-shaped stop element 13, in particular the stop element 13, engages the lengthwise fins 2e.

The housing 1, in particular the outer sleeve 1g, comprises, for example, a circumferential internal gear if at its proximal end, in which a clicking member 2f, which is made springy via an arm on the inner sleeve 2c, engages elastically. By rotation of the dose setting member 2 the clicking member 2f clicks over the teeth of the internal gear 1f, so that an acoustic and/or tactile signal is produced, which signals the setting of the dose. Furthermore, this results in the dose setting member 2 locking into a discrete position of angular rotation. In particular, the tooth pitch can be made so that the angular distance between two discrete angular positions corresponds to the angular distance between two adjacent scale values of a scale 10b of a dose display member 10 or a dose of one IU or one (1) unit or the smallest unit indicated on the scale 10b.

At its distal end the inner sleeve 2c comprises a third coupling structure 2b, which is designed as an internal gear. The inner sleeve 2c surrounds a sleeve-shaped drive member 4, which comprises a fourth coupling structure 4b in the form of an external gear, where the fourth coupling structure 4b and the third coupling structure 2b form a second coupling 2b, 4b, which is coupled if the actuation member 8 is unactuated, i.e., the third coupling structure 2b and the fourth coupling structure 4b mesh together non-rotatably, so that a rotation of the dose setting member 2 can be transmitted via the second coupling 2b, 4b to the drive member 4.

The drive member 4 comprises, in particular at its proximal end, a first coupling structure 4a in the form of an external gear. The rotational member 7 comprises, at its proximal end, a second coupling structure 7a in the form of an internal gear. The first coupling structure 4a and the second coupling structure 7a form a first coupling 4a, 7a, which is uncoupled if the actuation member 8 is unactuated, i.e., the first coupling structure 4a and the second coupling structure 7a are not in engagement, so that the drive member 4 can rotate relative to the rotational member 7.

The dose setting member 2, in particular the outer sleeve 2a, accommodates a spring housing 15, which is connected to the dose setting member 2 in an axially shiftable way and non-rotatably. On the one hand, the outer sleeve 2a and the spring housing 15 mesh together non-rotatably and axially shiftable, and on the other hand the arms 15a of the spring housing 15 that extend through the through-holes 2d produce a non-rotatable and axially shiftable connection between the spring housing 15 and the inner sleeve 2c. A rotation of the dose setting member 2, expressed in general terms, causes a rotation of the spring housing 15.

The spring housing 15 engages the drive member 4 in an axially fixed and rotatable way. A reset spring 9 acting as a compression spring and made as a helical spring is disposed between the spring housing 15 and the dose setting member 2. In particular, the reset spring 9 presses with its distal end against the inner sleeve 2c and with its proximal end against the spring housing 15, so that it presses the spring housing 15 and thus also the drive member 4 in the proximal direction. The reset spring 9 causes the first coupling 4a, 7a to be uncoupled and the second coupling 2b, 4b to be coupled when the actuation member 8 is unactuated. By shifting the spring housing 15 and thus the drive member 4 in the distal direction, first the first coupling 4a, 7a becomes coupled and then the second coupling 2b, 4b becomes uncoupled. The spring housing 15 has a sixth coupling structure 15b, which in this example is formed on the arm 15a, but could also be formed at a different location on the spring housing 15. The sixth coupling structure 15b can comprise an external gear. The housing 1 comprises, for example at its proximal end, a fifth coupling structure, for example in the form of an internal gear. The fifth coupling structure in this example is formed by the internal gear 1f, but basically speaking could also be formed separately from the internal gear 1f.

The fifth coupling structure if and the sixth coupling structure 15b form a third coupling 1f, 15b, which is uncoupled when the actuation member 8 is unactuated and coupled when the actuation member 8 is actuated. The third coupling 1f, 15b is designed with respect to the second coupling 2b, 4b, so that when the actuation member 8 is shifted from the unactuated position to the actuated position, said third coupling 1f, 15b becomes coupled before the second coupling 2b, 4b becomes uncoupled. In reference to the first coupling 4a, 7a, the third coupling 1f, 15b can be disposed so that, when the actuation member 8 is shifted from the unactuated position, said third coupling uncouples before, at the same time as, or after the coupling of the first coupling 4a, 7a. The reset spring 9 causes the third coupling 1f, 15b to be uncoupled when the actuation member 8 is unactuated.

The spring housing 15, in particular a sleeve-shaped section of the spring housing 15, surrounds a drive spring 5, which in this example acts as a rotational or torsion spring. The drive spring 5 is wound in a spiral from a ribbon-shaped material, for example spring steel, and surrounds a section of the drive member 4, which is in particular cone-shaped. One end of the drive spring 5 is connected non-rotatably to the spring housing 15, in particular to its sleeve-shaped section. The other end of the drive spring 5 is connected non-rotatably to the drive member 4, in particular its cone-shaped section. The drive spring 5 is tensioned highly enough that the spring energy stored in it is sufficient to completely release the product contained in the product container 6, in particular in several partial releases, without needing to be retensioned. The drive spring 5 thus supplies the drive member 4 with a torque that acts in the second rotation direction relative to the spring housing 15, which tries to rotate the drive member 4 in the second direction of rotation relative to the spring housing 15, or the housing 1. Because of the coupled second coupling 2b, 4b, a rotation of the drive member 4 relative to the spring housing 15 is blocked, so that rotation due to the drive spring 5 cannot yet take place.

The drive and metering apparatus comprises an actuation member 8 which can be shifted along the lengthwise axis L and non-rotatably relative to the housing 1 and which can be shifted along the lengthwise axis L from an unactuated position (FIG. 3c) to an actuated position (FIG. 5c) to trigger the release of a set product dose. The housing 1, in particular the outer housing 1g, forms a guide which guides the actuation member 8 non-rotatably and along the lengthwise axis L. In particular, a main segment 8c of the actuation member 8 is guided in the lengthwise direction by the housing 1. The main segment 8c is curved around the lengthwise axis L and extends only partly over the circumference of the housing 1. The main segment 8c is disposed inside the outer sleeve 1g. The outer sleeve 1g comprises a through-hole, through which a projection 8a formed on the main segment 8c and extending outward extends. The projection 8a projects above the outer surface of the outer sleeve 1g, so that the user can shift the projection 8a from the unactuated position to the actuated position, for example with a finger. The projection 8a can also be called the actuation section, since it serves as such. The actuation member 8, in particular the main section 8c, has a display device 8d distal to the actuation segment 8a, which comprises a window designed as a through-hole. The display device 8d can additionally comprise an arrow or a marking, for example a lug projecting into the window in the embodiment example that is shown, which points to a specific scale value, namely the selected one, which corresponds to the set product dose, out of several scale values of scale 10b of the dose display member 10 that are shown in window 8d.

The main section 8c of the actuation member 8 comprises an internal thread 8e or at least an internal thread section, which meshes in an external thread 10a on the outer circumference of the dose display member 10, which is formed as a dose display drum. The dose display member 10 comprises, on its outer circumference, a helical dose scale 10b, which comprises a plurality of successive scale values, which here comprise numbers in even number steps and, for example, line-shaped markings in the odd numbered steps. The pitch of the helical dose scale 10b corresponds to the pitch of the thread 10a. By rotating the dose display member 10 relative to the actuation member 8, the dose display member 10 is screwed along at the actuation member 8. Through this the dose scale 10b or the scale values of the dose scale 10b are moved under the display device 8d, so that the currently set product dose can be read by the user through the window 8d.

The dose display member 10 can be screwed back and forth between a position in which the zero dose is displayed in the display device 8d (zero dose position) and a maximum dose position in which the maximum dose value that can be released with one dosing is displayed in the display device 8d, for example 80 IU, in particular by rotating the dose setting member 2 back and forth in the first and section directions of rotation. The dose display member 10 comprises a zero dose stop 10d acting in the circumferential direction and a maximum dose stop 10c acting in the circumferential direction. In the zero dose position of the dose setting member 10, the zero dose stop 10d can abut a zero dose opposing stop 11c formed by the apparatus, which is formed in this example by a sliding sleeve 11. The sliding sleeve 11 is connected in an axially shiftable and non-rotatable way to the housing 1, in particular the outer sleeve 1g. For this the sliding sleeve 11 can comprise an engagement structure 11b, which engages an engagement structure, for example the gear 1f or an additional gear, on the inner circumference of the housing 1, in particular the outer sleeve 1g.

A maximum dose opposing stop 12a, against which the maximum dose stop 10c can abut in the maximum dose position, can be formed by a product container holder 12, which is preferably connected, for example snapped, to the housing 1, in particular the outer sleeve 1g, in a non-rotatable and axially fixed way.

The dose display member 10 and the drive member 4 mesh together non-rotatably and axially shiftable, so that a rotation of the drive member 4 causes a rotation of the dose display member 10. For this, at least one lengthwise guide 10f, which is in engagement with the drive member 4, is formed on the internal circumference of the dose display member 10.

The sliding sleeve 11, which can also be called the sliding member 11, and the actuation member 8 mesh together in an axially fixed way, so that the sliding sleeve 11 follows the axial movements of the actuation member 8 along the lengthwise axis L. The free end of the arms 15a is snapped to the sliding sleeve 11 in an axially fixed way, so that the spring housing 15 follows the axial movement of the sliding sleeve 11. The sliding sleeve 11 comprises an engagement structure 11b, which engages an engagement counter structure of the housing 1, in particular the outer sleeve 1g, in a non-rotatable and axially slidable way, so that the sliding sleeve 11 is non-rotatable and axially slidable with respect to the housing 1.

The stop element 13, e.g., stop ring, comprises an external thread 13a, which engages the internal thread 11a of the sliding member 11, so that the stop element 13 can be screwed along on the sliding sleeve 11. On its inner circumference the stop element 13 comprises at least one lengthwise guide 13b, which engages a corresponding lengthwise guide of the dose setting member 2, in particular its inner sleeve 2c, so that the stop element 13 is axially shiftable and non-rotatable with respect to the dose setting member 2. The stop element 13 is part of a device that prevents a dose from being set that exceeds the amount of product contained in the product container or released from it. The device comes into action only when the amount of product contained in the product container 6 or releasable from it is less than the maximum dose that can be set with the drive and metering apparatus. The stop element 13 comprises a stop 13c, which can abut an opposing stop 11d of the slidable sleeve 11.

The drive and metering apparatus of the first embodiment optionally comprises a device that indicates when the actuation member 8 is actuated (actuation marking) and/or the dose display member 10 is in its zero dose position (zero dose marking), independent of the display device 8d, which shows the currently set dose. For the actuation marking the main section 8c of the actuation member 8 comprises a wing extending in the circumferential direction from the main section 8c, on which a marking 8b is disposed. Alternatively, the wing can comprise a transparent region (not shown) distal or preferably proximal to the marking. In the unactuated position of the dose setting member 8 the marking is disposed under a viewing window 1e formed by the housing 1, in particular the outer sleeve 1g, so that the marking can be read through the viewing window 1e by the user. By shifting the actuation member 8 from the unactuated position to the actuated position, the marking 8b is shifted together with the actuation member 8, and the marking 8b is shifted from the position under the viewing window 1e so that it can no longer be read. In this way the transparent region moves into the viewing window 1e and protects the window, in particular the apparatus, from external intervention. The marking 8b is covered by a section of the outer sleeve 1g. The viewing window 1e is disposed offset at an angle and proximal to the actuation section 8a, so that the user of the apparatus will as far as possible not cover the viewing window 1e when actuating the actuation section 8a. Through this it additionally becomes possible for the user to visually establish if the actuation member 8 has been actuated.

For the zero dose marking the dose display member 10 comprises a marking 10e which is different than the dose display scale 10b, and which is disposed under the viewing window 1e in the zero dose position of the dose display member 10, so that the user of the display, when the actuation member 8 is actuated, is provided with a visual display of whether the dose display member 10 is in its zero dose position, independent of the scale values displayed in the display device 8d. Through the shifting of the actuation member 8 into the actuated position the marking 8b is shifted away from the viewing window 1e and the transparent region of the marking 8b protects the viewing window 1e. When a zero dose was set or when the product release has been completed, the marking 10e appears in the viewing window 1e under the transparent region. Through this the user obtains an additional indication of whether the product release was completely ended.

Alternatively, the marking 10e can be disposed under a window (not shown) of the dose setting member 2a, so that at a zero dose setting or at a completed product release the marking 10e appears in the window of the dose setting member 2a and the user is informed that the product release has taken place.

Basically speaking, it is possible to provide for the marking 10e a viewing window that is separated from the viewing window 1e (not shown).

In FIGS. 3a to 3d the injection apparatus is shown in an as-delivered or initial state. To use the apparatus the protective cap 14, which surrounds the product container holder 12, which covers a product container 6, which here is shown in the form of a cartridge, and a needle unit 16, which is mounted or can be attached at the distal end of the product container holder 12, is removed. The actuation member 8 is held in its unactuated position by means of the reset spring 9. The marking 8b is displayed in the viewing window 1e, through which it is additionally shown that the actuation member 8 is unactuated. The zero dose is displayed in the display device 8d.

To set the product dose to be released, the dose setting member 2 is turned relative to the housing 1 in a first direction of rotation to increase the dose, where the scale values indicated in the display device 8d count in the forward direction. To reduce the dose or to correct the dose the dose setting member 2 is turned in the direction of rotation opposite to the first direction of rotation, namely in a second direction of rotation, so that the scale values shown in the display device 8 count backward. The rotation of the dose setting member 2 is transmitted via the closed second coupling 2b, 4b to the drive member 4 and from the drive member 4 to the dose display member 10, which screws out in the distal direction, namely to the maximum dose opposing stop 12a, when the dose is increased, and screws in the proximal direction, namely toward the zero dose opposing stop 11c when the dose setting member 2 is rotated in the second direction of rotation. Alternatively, the dose display member 10, when increasing the dose, can screw in the proximal direction to the maximum dose opposing stop 12a and when reducing the dose can screw in the distal direction to the zero dose opposing stop 11c. Since when the actuation member 8 is unactuated, the spring housing 15 and the drive member 4 turn together with the dose setting member 2 and do not rotate towards each other, the drive spring 5 is neither tensioned nor relaxed. Because of the uncoupled first coupling 4a, 7a, the drive member 4 can rotate relative to the rotational member 7. Since the inner sleeve 2c rotates together with the outer sleeve 2a of the dose setting member 2 during dose setting, the stop element 13, when the dose has been increased or the dose setting member 2 is rotating in the first direction of rotation, is screwed toward the opposing stop 11d and when the dose setting member 2 is rotated in the second direction of rotation is screwed away from the stop 11d. The distance along the helical curve that the stop 13c has with respect to the zero dose opposing stop 11c is proportional to the amount of product contained in the product container 6 or that can be released from it. When the desired dose has been set, the actuation member 8 can be actuated.

In FIGS. 4a-4d the injection apparatus is shown set to the maximum dose, in which the maximally settable dose, which in this example is 80 IU, is displayed in the display device 8d. Since the amount of product contained in the product container 6 is greater than the maximum product dose that can be set with the drive and metering apparatus, the stop element 13 does not yet abut the zero dose opposing stop 11c. The maximum dose stop 10c (FIG. 2) abuts, for example, the maximum dose opposing stop 12a. To release the set product dose the actuation section 8a is shifted in the distal direction, so that the actuation member 8 is shifted in the distal direction from the unactuated position to the actuated position. In the shifting of the actuation member 8 in the distal direction the dose display member 10 likewise follows in the distal direction, where the display device 8d is shifted relative to the housing 1, but not relative to the dose display member 10. Through the shifting of the actuation member 8 the sliding sleeve 11 is carried along, which in turn carries along the spring housing 15 in the distal direction, and the spring housing 15 carries along the drive member 4 in the distal direction. The shifting of the drive member 4 and the spring housing 15 in the distal direction causes the first coupling 4a, 7a to be coupled first and then the second coupling 2b, 4b to be uncoupled, and the third coupling 1f and 15b becomes coupled. Further, through the shifting of the actuation member 8, the marking 8b is shifted away from the viewing window 1e. Alternatively, the transparent region (not shown) can be shifted into the viewing window 1e.

Because of the uncoupled second coupling 2b, 4b, the drive member 4 is now rotatable relative to the dose setting member 2, so that the drive spring 5 rotates the drive member 4 in the second direction of rotation relative to the dose setting member 2 and/or the housing 1. Through the rotation of the drive member 4 in the second direction of rotation, when the actuation member 8 is actuated, the inner sleeve 2c and the sliding sleeve 11 do not rotate relative to each other, so that the stop element 13 keeps or does not change its position in relation to the opposing stop 11d. Because of the closed first coupling 4a, 7a the rotational member 7 is rotated by the drive member 4 in the second direction of rotation, so that the rotation member 7 rotates the driven member 3 in the second direction of rotation, so that the driven member 3 becomes screwed in the distal direction because of the threaded engagement with the housing 1 and in doing so carries the piston accommodated shiftably in the product container 6 and shifts it in the distal direction, so that the product contained in the product container 6 is discharged through the needle.

When the actuation member 8 becomes released during the product release, it is returned from the actuated position to the unactuated position by the reset spring 9, where the second coupling 2b, 4b becomes coupled and the third coupling 1f, 15b becomes coupled, and the first coupling 4a, 7a becomes uncoupled. If the product release has not yet been completely completed, the dose that still needs to be discharged for complete product release is displayed in the display device 8d.

If the actuation member 8 is held in the actuated position before the end of the product release, which is achieved when the zero dose stop 10d abuts the zero dose opposing stop 11c, the marking 10e appears in the viewing window 1e, so that the end of the product release is visually displayed. Alternatively, the marking 10e can appear under the transparent region (not shown) or at any other place on the drive and metering apparatus. If the actuation section 8a becomes released, the actuation member 8 becomes reset to the unactuated position due to the reset spring 9, where the marking 8b appears in the viewing window 1e.

Now new dose settings and product releases can be carried out in correspondence with the above function.

In FIGS. 6a to 6d the apparatus is shown after the complete release of the amount of product contained in the product container 6 or releasable therefrom, where the stop element 13 abuts by means of its stop 13c against the opposing stop 11d. An attempt to rotate the dose setting member 2 relative to the housing 1 in this state causes the stop element 13 to press against the opposing stop 11d, so that the rotation of the inner sleeve 2c in the first direction of rotation is blocked and thus the rotation of the outer sleeve 2a is also blocked. Generally, the dose setting member 2 can thus no longer be rotated in the first direction of rotation. A rotation of the dose setting member 2 in the second direction of rotation, which would cause a reduction of the set dose, is indeed basically permitted by the stop element 13, but prevented by the zero dose stop 10d and the zero dose opposing stop 11c which abut one another. Thus, the dose setting member 2 cannot be rotated in either of the two directions of rotation. The apparatus can now be thrown away.

The second embodiment of an injection apparatus with the drive and metering apparatus according to the invention, which is shown in FIGS. 7 to 11b, comprises an elongated housing 101. A product container holder 112, in which a product container 106, in this example a cartridge, is accommodated, is disposed at the front or distal end of the housing 101. A needle unit 116 is disposed at the distal end of the cartridge 106 or the product holder container 112 where the preferably liquid product or medicament contained in the product container 106 can be discharged through the needle of the needle unit 116.

The product container holder 112 and optionally the needle unit 116 are covered by a removable cap 114, which is separably attached at the product container holder 112, in particular is snapped on. The drive and metering apparatus forms, for example with the product holder 106 and product holder container 112 mounted on the drive and metering apparatus, an injection apparatus.

The housing 101 is a multicomponent housing. It comprises an outer sleeve 101a, a first housing insert 101b and a second housing insert 101c, as can best be seen from FIG. 8b. Optionally the housing inserts 101b, 101c could be made in one piece with the outer sleeve 101a, so that the housing 101 is a monolithic component, where the assembly of the apparatus, however, is easier with a multicomponent housing.

A rotational member 107 is disposed in the housing 101 rotatable and axially fixed. In particular, the housing 101 and the rotational member 107 mesh together so that the rotational member 107 is rotatable and axially fixed relative to the housing 101. The rotational member 107 could basically be a single component, but in this example it comprises a plurality of parts, namely a coupling sleeve 107a and a threaded sleeve 107b, which are connected together non-rotatably and axially fixed, in particular are snapped together. In this way the parts can be made of different materials. An annular slot is formed between the coupling sleeve 107a and the threaded sleeve 107b, in which the first housing insert 101b engages, so that the rotational member 107 is rotatable and axially fixed relative to the housing 101. The rotational member 107, in particular the threaded sleeve 107b, comprises an internal thread 107d, which engages in an external thread 103c of a threaded rod 103a, which is a part of a driven member 103. The threaded rod 103a comprises at least one lengthwise guide, in particular a lengthwise slot 103d, which overlaps the external thread 103c and extends along the lengthwise axis L of the drive and metering apparatus. The distal end of the threaded rod 103a is connected to a plate-shaped flange 103b, for example made in one piece or snapped on, so that the flange 103b is, for example, freely rotatable with reference to the threaded rod 103a. The flange 103b and the threaded rod 103a form the driven member 103. The housing 101 engages the guide slot 103d, so that the driven member 103 is non-rotatable and axially shiftable relative to the housing 101. In order to move the driven member in the distal direction for product release, so that the piston in the product container 106 is shifted in the distal direction, the rotation member 107 is rotated in a second direction of rotation, so that the threaded rod 103 is screwed along on the rotational member 107 and is shifted in the distal direction with the housing 101 because of the lengthwise guide.

A unidirectional coupling, which permits a rotation of the rotational member 107 in the second direction of rotation and does not permit or blocks a rotation of rotational member 107 in the first direction of rotation, which is opposite the second direction of rotation, is formed between the rotational member 107 and the housing 101. The unidirectional coupling can also be called a ratchet. The unidirectional coupling comprises a ratchet member 117, which is connected non-rotatably with the rotational member 107, in particular the coupling sleeve 107a. The ratchet member 117 comprises a rear gear 117a, which comprises a plurality of sawtooth-shaped teeth and engages in a counter gear, which comprises a plurality of sawtooth-shaped teeth, of housing 101, in particular the housing insert 101b. Because of the sawtooth-shaped teeth, the ratchet member 117 can rotate in the second direction of rotation relative to the housing 101 and cannot rotate in the first direction of rotation relative to the housing. The ratchet member 117 is axially movable relative to the rotational member 107, in particular relative to the coupling sleeve 107a. The rotational member 107, in particular the coupling sleeve 107a, comprises an external gear 107f, in which an internal gear 117b of the ratchet member 117 meshes non-rotatably and axially shiftable. The section of the ratchet member 117 that comprises the gears 117a and 117b, abuts axially and elastically against the coupling sleeve 107a of the rotational member 107. This can take place by means of a separate compression spring formed between the said section and the coupling sleeve 107a or, as shown here, by means of a spring section 117c, which occurs at the section that forms the gears 117a and 117b. Thus, the section that forms the gears 117a and 117b can be shifted in the proximal direction against the spring force of the spring section 117c.

If the rotational member 107 is rotated in the second direction of rotation, the rear gear 117a clicks over the opposing gear of the housing 101 or the first housing insert 101b, thus producing clicking sounds. However, rotation in the opposite direction, namely in the first direction of rotation, is prevented.

A dose setting member 102, which is rotatable and axially fixed with respect to the housing 101 is disposed at the proximal end of the housing 101. The dose setting member 102 circumferentially surrounds the proximal end of the housing 101. The dose setting member 102 is closed at its proximal end and forms the proximal end of the drive and metering apparatus. The dose setting member 102 comprises, on its inner circumference, an annular slot, in which a projection of the outer circumference of the housing 101 engages, so that the dose setting member 102 is rotatable and axially fixed with respect to the housing 101. The dose setting member 102 is rotated relative to the housing 101 to set a dose, in particular in a first direction of rotation to increase a dose to be released and in a second direction of rotation to reduce or release the dose to be released, the second direction of rotation being opposite the first direction of rotation.

A sleeve-shaped drive member 104, which surrounds the threaded rod 103a or the driven member 103, is disposed in the housing 101, in particular the outer sleeve 101a. The drive member 104 is, with respect to the housing 101, axially shiftable along the lengthwise axis L and rotatable about the lengthwise axis L. The dose setting member 102 and the drive member 104 are connected to each other non-rotatably and axially shiftable or meshed together non-rotatably and axially shiftable, so that the drive member 104 follows the rotary movement of the dose setting member 102 and vice versa.

The drive and metering apparatus comprises a sleeve-shaped display member 110, which is designed as a dose display drum and surrounds the drive member 104. The dose display member 110 comprises, on its outer circumference, a thread 110a and a dose scale 110b. The dose scale 110b comprises a plurality of helical, successive scale values, which together produce the spiral dose scale 110b, as in the first embodiment. The spiral dose scale 110b and the thread 110a have the same pitch.

The drive and metering apparatus comprises an actuation member 108 (FIGS. 8a, b) which is non-rotatable about the lengthwise axis L with respect to the housing 101 and is axially shiftable along the lengthwise axis L. In particular, the actuation member 108 engages the housing 101 so that it is non-rotatable and axially shiftable. The actuation member 108 comprises at least one threaded section, in particular an internal thread 108e, which engages the external thread 110a of the dose display member 110, so that the dose display member 110 can be screwed along on the actuation member 108 when the dose display member 110 is rotated about the lengthwise axis L. The dose display member 110 is connected non-rotatably and axially shiftable to the drive member 104, in particular directly or indirectly, as for example via a sleeve-shaped intermediate member 111, which can also be called an intermediate sleeve, as shown in the second embodiment example. The drive member 104 and the intermediate member 111 mesh with each other non-rotatably and axially shiftable about the lengthwise axis L, so that the intermediate member 111 follows the rotary movement of the drive member 104 and can be shifted along the lengthwise axis L relative to the drive member 104. The intermediate member 111 and the dose display member 110 mesh with each other so that they are non-rotatable about the lengthwise axis L and can be shifted along the lengthwise axis L, so that the dose display member 110 follows the rotary movement of the intermediate member 111 and can be shifted along the lengthwise axis L relative to the intermediate member 111. Thus, a rotation of the dose setting member 102 in the first direction of rotation causes a rotation of the dose display member 110, likewise in the first direction of rotation, and a rotation of the dose setting member 102 in the second direction of rotation likewise causes a rotation of the dose display member 110 in the second direction of rotation. Through the rotation of the dose setting member 102 in the first direction of rotation the dose display member 110 is screwed in the proximal direction, and through the rotation of the dose setting member 102 in the second direction of rotation the dose display member 110 is screwed in the distal direction.

The actuation member 108 comprises an elongated main section 108c, which is curved around the lengthwise axis L and extends over a part of the circumference and in particular is disposed outside the outer sleeve 101a and from which an actuation section 108a projects outward, in order, for example, to be able to be shifted by a finger of the user of the apparatus, in order to be able to shift the actuation member 108 from an unactuated position (FIG. 8a) in the distal direction into an actuated position (FIG. 10a). The actuation member 108, in particular its main section 108c, comprises a display device 108d, which in this example is made as a window or through-hole and through which a currently set and to be released product dose can be read from the dose scale 110b. By shifting the actuation member 108 along the lengthwise axis L the dose display member 110 is carried along the lengthwise axis L because of the threaded engagement.

The actuation section 108a is disposed proximal and along the lengthwise axis L in an alignment with the display device 108d. The main section 108c, at its distal end, engages the outer sleeve 101a through a through-hole in the circumferential direction under the outer sleeve 101a and thus ensures that the actuation member 108a will not fall out at its distal end. At the proximal end the actuation member 108 comprises a tongue-shaped section, which grips the outer sleeve 101a and/or the dose setting member 102 at the inner side, so that the proximal end of the actuation member 108 is secured against falling out.

The actuation member 108 is pressed into the unactuated position (FIG. 8a) by a reset spring 109, which in this example is made as a helical spring and acts as a compression spring along the lengthwise axis L. The spring 109 is compressed or tensioned through the actuation of the actuation member 108 from the unactuated to the actuated position. The reset spring 109 abuts at its proximal end a coupling member 115, in particular a coupling sleeve, where the coupling member 115 couples the proximal end of the reset spring 109 to the actuation member 108 in an axially fixed way. The coupling member 115 is connected axially fixed to the actuation member 108, in particular the main section 108c. Optionally, the actuation member 108 and the coupling member 115 could be formed together in one piece, where a two-part design offers advantages in assembly.

The distal end of the reset spring 109 abuts, in particular directly, specifically via the coupling member 118, which can, for example, be formed as a coupling ring, against the housing 101, for example against the first housing inset 101b.

The ring-shaped coupling member 118 comprises at its distal end a rear engagement structure 118b, in particular a circular gear, which engages in an engagement counter structure 101d, which is disposed on housing 101, in particular on the first housing insert 101b pointing in the proximal direction. The engagement structures 101d and 118b are shaped so that a lower torque is needed to rotate the coupling member 118 in the first direction of rotation relative to the housing 101 at the coupling member 118 than is necessary for rotation in the second direction of rotation. This can be achieved by having the gear flanks of the engagement structure 118b that point in the first direction of rotation and/or the gear flanks of the engagement structure 101d that point in the second direction of rotation made flatter than the gear flanks of the gear 118b pointing in the second direction of rotation and/or the gear flanks of the engagement structure 101d pointing in the first direction of rotation.

A drive spring 105, which is made as a helical spring and which acts as a torsion spring, is disposed between the intermediate member 111 and the housing 101. The proximal end of the drive spring 105 abuts against the second housing insert 101c or generally against the housing 101, where the distal end of the drive spring 105 abuts against the intermediate member 111. By rotating the dose setting member 102 in the first direction of rotation the drive spring 105 becomes tensioned and by rotating the dose setting member 102 in the second direction of rotation the drive spring 105 becomes relaxed.

The intermeshing engagement structures 101d and 118b are provided to keep the drive spring 105 from relaxation when the dose setting member 102 is released. The torque acting from the drive spring 105 to the coupling member 118 is, in particular in the case in which the maximum settable dose has been set, less than the torque that is necessary to rotate the coupling member 118 in the second direction of rotation. This guarantees that the spring 105 cannot unintentionally become relaxed. The holding torque that is necessary to rotate the coupling member 118 in the first direction of rotation relative to the housing 101 is dependent not only on the design of the engagement structure 101d and 118b, but also on the choice of the strength of the spring and/or the tensioning of the reset spring 109.

The coupling structure 118 comprises, on its inner circumference, a third coupling structure 118a, which is made as an internal gear. The drive member 104 comprises, on its outer circumference, a fourth coupling structure 104b, which is made as an external gear and which engages in the third coupling structure 118a when the actuation member 108 is in its unactuated position. The coupling member 118 and the drive member 104 mesh together non-rotatably and axially shiftable when the actuation member 108 is in its unactuated position. The third coupling structure 118 and the fourth coupling structure 104 form a second coupling 104b, 118a.

The drive member 104 comprises a first coupling structure 104a, which is designed as an internal gear. The rotational member 107, in particular the coupling sleeve 107a, comprises a second coupling structure 107c, which is made as an external gear and which engages in the first coupling structure 104a when the actuation member 108 is actuated, and does not engage when the actuation member 108 is not actuated.

The first coupling structure 104a and the second coupling structure 107c form a first coupling 104a, 107c. The actuation member 108 is coupled or connected to the drive member 104 axially fixed in particular via the coupling member 115. In particular, the coupling member 115 engages the drive member 104 axially fixed and rotatably. The actuation member 108 and the coupling member 115 are in an axially fixed, in particular also non-rotatable engagement.

The drive and metering apparatus of the second embodiment comprises a mechanism, which prevents the setting of a dose that exceeds the amount of product contained in the product container 106 or releasable from it. Said mechanism comprises a sleeve-shaped stop element 113, which comprises an internal thread 113a, which engages the external thread 103c of the threaded rod 103a. The drive member 104 surrounding the stop element 113 and the stop element 113 mesh together non-rotatably and axially shiftable, so that the stop element 113 follows the rotations of the drive member 104. The stop element 113 comprises a stop 113b, which can abut against an opposing stop 107e, which is formed by the rotational member 107, in particular the coupling sleeve 107a. The space between the stop 113b and the opposing stop 107e that extends along a helical curve is proportional to the amount of product contained in the product container 106 or releasable from it.

The dose display member 110 comprises a zero dose stop 110d acting in a circumferential direction and a maximum dose stop 110c acting in the circumferential direction. The coupling member 115 comprises a zero dose opposing stop 115a, against which the zero dose stop 110d is pressed when an attempt is made to set a dose that is less than zero. The housing 101, in particular the second housing insert 101c, comprises a maximum dose opposing stop 101e, against which the maximum dose stop 110c is pressed when an attempt is made to set a dose that is greater than the maximum settable dose, for example 80 IU. In the zero dose position the zero dose is displayed in the display device 108d, and in the maximum dose position the maximum product dose that can be set with the apparatus, 80 IU here, is displayed in the display device 108d. The dose display member 110 can be screwed back and forth between the zero dose position and the maximum dose position, in particular by back and forth rotation of the dose setting member 102 in the first and second directions of rotation.

The drive and metering apparatus of the second embodiment optionally comprises a device that signals when the actuation member 108 is actuated (actuation marking) and/or the dose display member 110 is in its zero dose position (zero dose marking), independent of the display device 108d, which displays the currently set dose. For the actuation marking the main section 108c of the actuation member 108 can have a wing (not shown) extending from the main section 108c, on which a marking can be disposed. Alternatively, the wing can comprise, besides the marking, a transparent region (not shown). In the unactuated position of the dose setting member 108 the marking can be disposed under a viewing window (not shown) formed by the housing 101, in particular the outer sleeve 101a, so that the marking can be read by the user through the viewing window. By shifting the actuation member 108 from the unactuated position to the actuated position the actuation marking can be shifted together with the actuation member 108, where the actuation marking is shifted from the position under the viewing window, so that it can no longer be read. In this case the transparent region (not shown) can be shifted into the viewing window and the window can protect, in particular, the apparatus from external intrusions. The actuation marking becomes covered by a section of the outer sleeve 101a. The viewing window can be disposed at an angular offset and distal and/or proximal to the actuation section 108a, so that the user of the apparatus is unlikely to cover the viewing window when the actuation section 108a is actuated. This additionally allows the user to establish visually if the actuation member 108 is actuated.

For a zero dose marking the dose display member 110 can comprise a marking (not shown) that is different from the dose display scale 110b, which marking is disposed in the zero dose position of the dose display member 110 under the viewing window, so that the user of the apparatus can, if the actuation member 108 is actuated, visually see if the dose display member 110 is in its zero dose position, independent of the scale value displayed in the display device 108d. By shifting the actuation member 108 into the actuated position the actuation marking can be shifted out of the viewing window, in which case the transparent region of the actuation marking appears in the viewing window. If a zero dose was set or if the product release has taken place, the zero dose marking will be visible in the viewing window, under the transparent region, in which case the zero dose marking is overlain by the transparent region. Alternatively, the transparent region can comprise pigments or patterns, which form a zero dose marking in the overlain position together with the differentiated marking of the dose display scale 110a. Through this the user obtains a display indicating if the product release was completely ended. Alternatively, the marking can be disposed under a window of the dose setting member 102, so that at a zero dose setting or if the product release has taken place, the zero dose marking appears in the window of the dose setting member 102 and the user is informed that the product release has taken place.

Various views of the injection apparatus are shown in a starting or as-delivered state in FIGS. 8a to 8d. For setting and administration of a product dose, the cap 114 is removed and a dose is set by rotating the dose setting member 102 relative to the housing. To increase the dose the dose setting member 102 is rotated in a first direction of rotation, and to decrease a dose it is rotated in the second direction of rotation. During dose setting the actuation member 108 is unactuated. Optionally, the actuation marking can be displayed in the viewing window (not shown), so that it can be seen that the actuation member 108 is unactuated. The currently set product dose can be read through the display device 108d. If the actuation member 108 is unactuated, the first coupling 104a, 107c is uncoupled and the second coupling 104b, 118a is coupled. In this way the drive member 104 can be rotated relative to the rotational member 107 without the rotational member 107 following the drive member 104. Upon a dose increase, i.e., during the rotation of the dose setting member 102 in the first direction of rotation, the drive spring 105 becomes tensioned and upon a reduction of the dose, i.e., during the rotation of the dose setting member 102 in the second direction of rotation, it becomes untensioned. Upon a reduction of the dose the coupling member 118, in particular the gear 118b, clicks over the engagement structure 101d of the first housing insert 101b in the second direction of rotation since, in addition to the torque of the drive spring 105, the torque applied by the user on the dose setting member 102 in the second direction of rotation acts on the coupling member 118.

During the dose setting, when the drive member 104 rotates relative to the driven member 103, the stop element 113, which rotates with the drive member 104, screws along on the threaded rod 103a. In the rotation of the dose setting member 102 in the first direction of rotation the stop element 113 is screwed in the distal direction on the threaded rod 103a, so that the distance between the stop 113b and the opposing stop 107e is reduced. When the dose setting member 102, in the case of dose correction or if the first coupling 104a, 107c is uncoupled, is rotated in the second direction of rotation, the stop element 113 is screwed along in the proximal direction on the threaded rod 103a, so that the distance between the stop 113b and the opposing stop 107e becomes greater.

The injection apparatus is shown set to the maximum dose in FIGS. 9a and 9b, where the actuation member 108 is unactuated. To release the set product dose the actuation member 108 is shifted from the unactuated position in the distal direction to the actuated position by actuating the actuation section 108a, so that the release of the set dose is triggered. Further, through the shifting of the actuation member 108, the actuation marking (not shown) is shifted from the viewing window and a transparent region (not shown) appears in the viewing window.

The injection apparatus, which is in the maximally dosed state, is shown in FIGS. 10a and 10b with an actuated actuation member 108. Through the actuation of the actuation member 108, the dose display member 110 is carried along because of the threaded engagement of the actuation member 108, i.e., is shifted along the lengthwise axis L, initially without rotational movement. The shifting of the actuation member 108 into the actuated position causes the coupling member 115 to be carried from the actuation member 108, so that the reset spring 109 is compressed. If the user releases the actuation member 108, the reset spring 109 returns the actuation member 108 from the actuated position to the unactuated position.

The shifting of the actuation member 108 into the actuated position causes, via the coupling member 115, the drive member 104 to travel along or shift in the distal direction, so that first the first coupling 104a, 107c becomes coupled and then, i.e., only when the first coupling 104a, 107c is coupled, the second coupling 104b, 118a becomes uncoupled. A transfer of torque from the drive member 104 to the rotational member 107 takes place via the coupled first coupling 104a, 107c. Through the uncoupling of the second coupling 104b, 118a the drive member 104 becomes released for a rotation in the second direction of rotation because of the torque of the tensioned drive spring 105, so that the drive member 104 rotates in the second direction of rotation, so that the rotational member 107 likewise is rotated in the second direction of rotation. In this way the driven member 103 shifts in the distal direction and carries the piston in the product container 106 along, so that the product is released through the needle of the needle unit 116. During the product release, or rotational movement of the drive member 104, the dose display member 110 becomes screwed up to the zero dose opposing stop 115a of the coupling member 115 and clicking sounds are generated by the ratchet member 117.

Since the driven member 103 and the drive member 104 rotate together about the lengthwise axis and do not rotate relative to each other during the product release, i.e., when the first coupling 104a, 107e is coupled, the stop element 113 retains its axial position with reference to the drive member 104, and the threaded rod 103a is screwed by the stop element 113 in the distal direction. The distance between the stop 113b and the opposing stop 107e does not change during the product release.

The release of the set product dose is ended when the zero dose stop 110d abuts the zero dose opposing stop 115a. If the actuation member 108 is held in the actuated position up to the end of the product release, the zero dose marking (not shown) can appear in the viewing window (not shown), so that the end of the product release is visually displayed. If the actuation segment 108a is released, the actuation member 108 is returned to the unactuated position by the reset spring 109, and the actuation marking appears in the viewing window. Now the dose setting and dose release can be repeated, provided there is still sufficient product in the product container 106.

During the product release the dose setting member 102 rotates along in the second direction of rotation. Optionally, an additional coupling (not shown) could be provided between the drive member 104 and the dose setting member 102, which becomes uncoupled if the actuation member 108 is uncoupled and becomes coupled through the actuation of the actuation member 108, which results in the dose setting member 102 not rotating together with the drive member 104 during the product release. Additionally optionally, still another additional coupling could be provided between the dose setting member 102 and the housing 101 or a housing-fixed element, the additional coupling being uncoupled if the actuation member 108 is unactuated and coupled if the actuation member 108 is actuated, so that the dose setting member 102 is non-rotatable relative to the housing during the product release and is rotatable relative to the housing 101 during dose setting.

If the amount contained in the product container is less than the maximum settable dose and an attempt is made to set a dose that is greater than the amount of product contained in the product container 106 or that can be released from it, the stop element 113, in particular the stop 113b, becomes pressed against the stop 107e of the rotational member 107, which acts in the circumferential direction, when an attempt is made to rotate the dose setting member 102 in the first direction of rotation. Since the rotational member 107 cannot be rotated in the first direction of rotation relative to the housing 101 because of the ratchet member 117, a rotation of the drive member 104 and thus the dose setting member 102 in the first direction of rotation is blocked, so that a further dosing is not possible, even if basically speaking a higher dose could be set with the injection apparatus.

The injection apparatus is shown at the end of the release of the total dose contained in the product container 106 in FIGS. 11a and 11b. The setting of a further dose is no longer possible here, because of the stop element 113, which abuts the rotational member 107.

A modification of the triggering member 8 or 108, in particular for the first and second embodiments, is shown in FIGS. 12a and 12b. For the sake of clarity, only reference numbers for the second embodiment are given in the following description, where the figures contain the reference numbers for the first and second embodiments.

The triggering member 108 has a main section 108c, e.g., main segment, which is disposed outside the outer sleeve 101a of the housing 101. From the main section 108c, which comprises the viewing device 108d, in particular the window, two wings project in the circumferential direction on both sides and surround the outer sleeve 101a over its outer circumference, in particular the greater portion of the circumference. Each of the wings has an actuation segment 108a, which is disposed about the lengthwise axis L at an angular offset to the display device 108d. Through this arrangement the actuation member 108 can be easily actuated with the thumb and/or index finger of the hand gripping the outer sleeve 101a without covering the display device 108d.

Figure 14C:
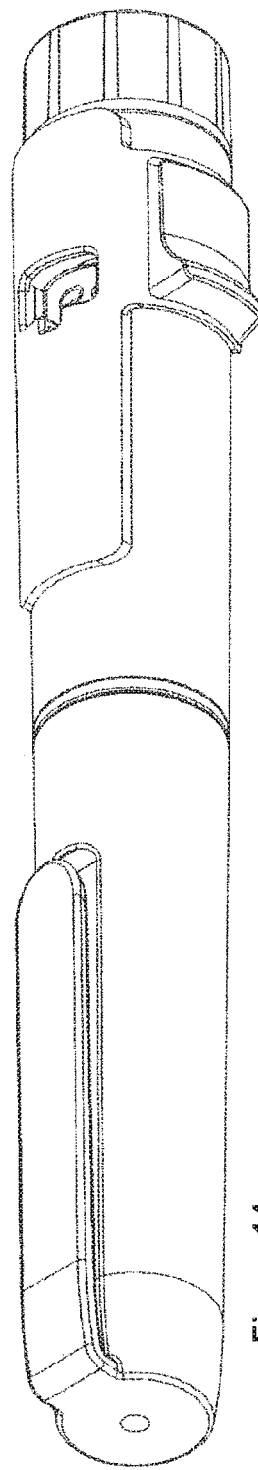
FIG. 14c shows a perspective view of the fifth embodiment of an injection apparatus.
Figure 14A:
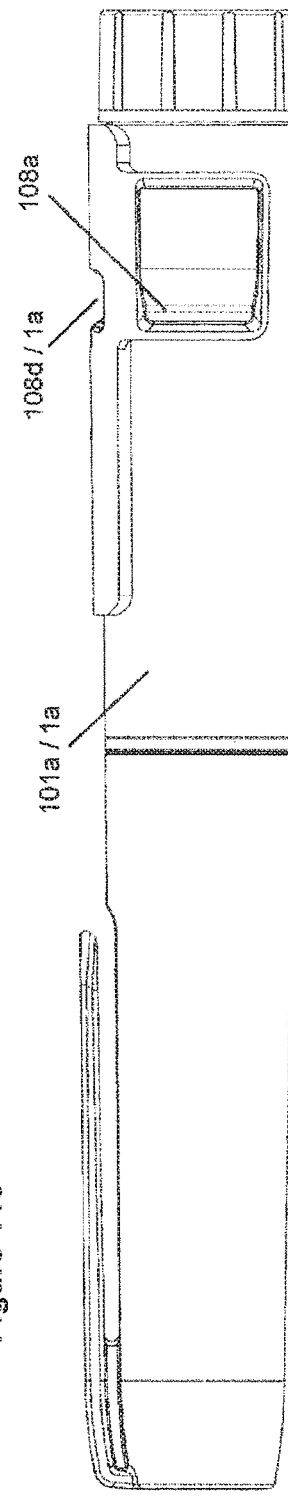
FIGS. 14a and 14b show views of an injection apparatus according to a fifth embodiment that are rotated 90° with respect to each other about the lengthwise axis.
Figure 14B:
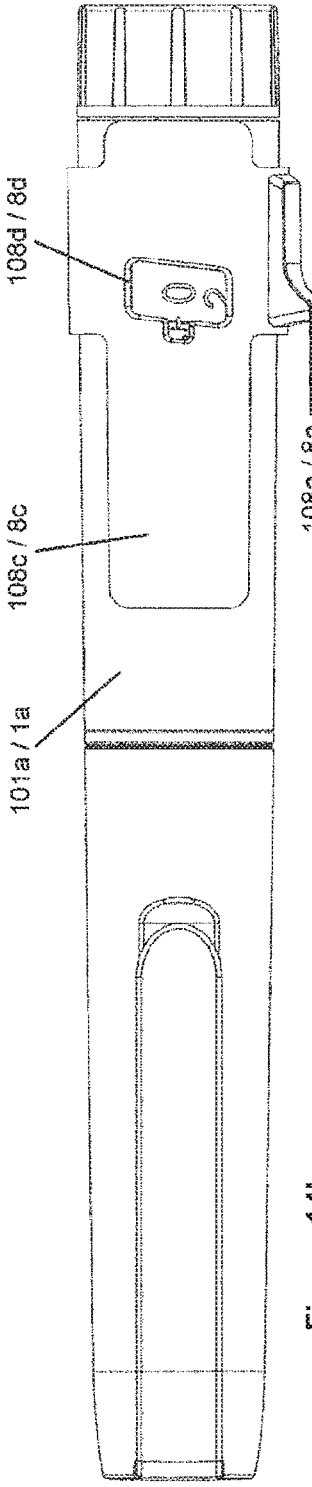

FIGS. 14a and 14b show a modification of the embodiment from FIGS. 12a and 12b, where only one of the wings has a triggering member 108a and the other does not. In this embodiment the actuation section 108a can, for example, be actuated with the thumb of the hand gripping the outer sleeve 101a without covering the display device 108d.

FIGS. 13a and 13b show another modification of the actuation member 108, where the main section 108c of the actuation member 108, which comprises the viewing device 108d, in particular the window, is disposed outside the outer sleeve 101a, in particular on its outer circumference. The actuation section 108a is disposed distal to the display device and in an alignment with the display device 108d along the lengthwise axis L. In this way the actuation section 108a can be actuated, for example, with the thumb of the hand that grips the outer sleeve 101a without covering the display device 108d.

FIGS. 15a and 15b show another modification of the actuation member 108, where the main section 108c, which comprises the display device 108d, is disposed within the outer sleeve 101a, in particular on its inner circumference. The actuation element 108 comprises a ring-shaped actuation section 108a, which is disposed outside the outer sleeve 101a and surrounds the outer sleeve 101a over its outer circumference. The ring-shaped actuation section 108a is connected to the main section 108c via a connecting bridge, which grips through the outer sleeve 101a. For this the outer sleeve 101a can comprise, for example, a slot-shaped recess, through which the bridge extends, which connects the ring-shaped actuation section 108a and the main section 108c, which forms the display device 108d. The slot-shaped recess can serve at the same time as a lengthwise guide, i.e., as a rotation lock, for the actuation member 108a.

The ring-shaped actuation section 108a can be gripped by the user of the apparatus in various positions, so that user comfort is improved and at the same time the user cannot cover the display device 108d with a part of the hand that grips the outer sleeve 101a. The actuation section 108a is disposed proximal to the display device 108d, but could also be disposed distal to the display device 108d.

For example, the actuation section 108a can be gripped by the user of the apparatus with the hand, and in this case he no longer grips the outer sleeve 101a. By pressing the injection apparatus at the injection site a "push-on-skin" release can be realized, in which the gripping hand grips the actuation member 108, in particular the actuation section 108a, and shifts it in the distal direction. For this function the actuation section 108a can also comprise a different shape, for example a sleeve-shape, so that the actuation section 108a can be gripped even better.

What is claimed is:

1. A drive and metering apparatus for an injection apparatus for release of a liquid product, the drive and metering apparatus having a distal end where the liquid product is dispensed, and a proximal end, which is opposite the distal end, the drive and metering apparatus comprising:
   a) a housing extending along a lengthwise axis of the drive and metering apparatus;
   b) a dose setting member configured to rotate relative to the housing around the lengthwise axis for setting the product dose to be released;
   c) an actuation member configured to shift axially and non-rotatably relative to the housing along the lengthwise axis from an unactuated position, which it takes during the setting of the product dose to be released, to an actuated position, which it takes during product release, wherein shifting of the actuation member into the actuated position triggers the product release, and the actuation member comprises an actuation section to which a user of the drive and metering apparatus has access and by which the user can shift the actuation member from the unactuated position to the actuated position, and wherein the actuation section is disposed distal to the dose setting member; and
   d) a dose display member, wherein the dose display member, in the unactuated position of the actuation member, is coupled to the dose setting member such that a rotation of the dose setting member causes a rotation of the dose display member, and wherein the actuation member is coupled to the dose display member such that the dose display member is shifted axially and non-rotatably relative to the housing along the lengthwise axis by the actuation member when the actuation member is shifted from the unactuated position to the actuated position.

2. The drive and metering apparatus of claim 1, wherein the actuation section is disposed between the dose setting member and the distal end of the drive and metering apparatus.

3. The drive and metering apparatus of claim 2, wherein the dose setting member is disposed before the proximal end of the drive and metering apparatus and forms the proximal end of the drive and metering apparatus.

4. The drive and metering apparatus of claim 1, wherein the housing comprises a viewing window, and the actuation member comprises a marking disposed within the housing, wherein the marking is disposed on the actuation member such that in the unactuated position of the actuation member the marking is disposed relative to the viewing window such that the marking can be read through the viewing window, and wherein the marking is shifted by the shifting of the actuation member into the actuated position into a position relative to the viewing window such that the marking can no longer be read through the viewing window.

5. The drive and metering apparatus of claim 1, further comprising a display device formed by the actuation member, wherein in the unactuated position of the actuation member, and during rotation of the dose setting member, a scale value of a dose display scale disposed on an outer circumference of the dose display member can be read through the display device.

6. The drive and metering apparatus of claim 5, wherein the housing comprises a viewing window and the dose display member comprises a zero dose marking disposed within the housing, the zero dose marking differing from the dose display scale, wherein when the set dose is zero or the set dose has been completely administered, and when the actuation member is in the actuated position, the zero dose marking is disposed on the dose display member such that the zero dose marking is positioned with respect to the viewing window such that the zero dose marking can be read through the viewing window.

7. The drive and metering apparatus of claim 5, wherein the drive and metering apparatus comprises a viewing window, the actuation member comprises a transparent region, and the dose display member comprises a marking different from the dose display scale, wherein the transparent region overlies the different marking and forms a zero dose marking, and when the set dose is zero or the set dose was completely administered and the actuation member is in the actuated position, the zero dose marking can be read through the viewing window.

8. The drive and metering apparatus of claim 7, wherein the actuation section is disposed proximal or distal to the display device.

9. The drive and metering apparatus of claim 7, wherein the actuation section is at a same angular position in the circumferential direction or about the lengthwise axis (L) as the display device, or the actuation section is disposed in the circumferential direction or about the lengthwise axis (L) at an angular offset to the display device.

10. The drive and metering apparatus of claim 5, wherein the housing comprises a through-hole through which the actuation section projects,
wherein the actuation section projects from a main section of the actuation member disposed within the housing, the main section of the actuation member forming the display device, which extends through the through-hole, and a free end of the actuation section projects beyond an outer circumference of the housing.

11. The drive and metering apparatus of claim 5, wherein the housing comprises a through-hole through which the actuation section projects, wherein the actuation section projects outward from a main section of the actuation member which is disposed outside the housing and forms the display device.

12. The drive and metering apparatus of claim 5, wherein the dose display member comprises an external thread and the actuation member comprises an internal thread that engages the external thread of the dose display member in a threaded engagement, wherein the dose display member is configured to be screwed along the actuation member by the threaded engagement, and wherein the actuation member carries the dose display member axially by the threaded engagement when the actuation member is shifted to the actuated position.

13. The drive and metering apparatus of claim 1, wherein the actuation member partly surrounds the housing over a circumference of the housing or completely surrounds the housing.

14. The drive and metering apparatus of claim 1, further comprising:
a driven member accommodated in the housing;
a drive member rotatable relative to the housing, wherein during the product release the drive member is coupled to the driven member such that a rotation of the drive member causes the driven member to be moved in the distal direction relative to the housing; and
a drive spring which the drive member can drive in a rotating motion and which releases stored kinetic energy to the drive member.

15. The drive and metering apparatus of claim 14, further comprising a first coupling disposed between the drive member and the driven member, wherein the first coupling is uncoupled during the setting of the product dose, which enables the drive member to be rotated relative to the driven member, wherein the first coupling becomes coupled by the shifting of the actuation member into the actuated position.

* * * * *

UNITED STATES PATENT AND TRADEMARK OFFICE
CERTIFICATE OF CORRECTION

PATENT NO. : 11,229,748 B2
APPLICATION NO. : 16/109192
DATED : January 25, 2022
INVENTOR(S) : Streit et al.

It is certified that error appears in the above-identified patent and that said Letters Patent is hereby corrected as shown below:

In the Specification

In Column 16, Line 28 after circumferential internal gear delete ""if"" and replace with -- $1f$ --

In Column 17, Line 32 after fifth coupling structure delete ""if"" and replace with -- $1f$ --

Signed and Sealed this
Nineteenth Day of April, 2022

Katherine Kelly Vidal
*Director of the United States Patent and Trademark Office*